(12) United States Patent
Mills

(10) Patent No.: US 10,963,838 B2
(45) Date of Patent: *Mar. 30, 2021

(54) METHODS USING MULTI-DIMENSIONAL REPRESENTATIONS OF MEDICAL CODES

(71) Applicant: 3M INNOVATIVE PROPERTIES COMPANY, St. Paul, MN (US)

(72) Inventor: Ronald E. Mills, Florence, OR (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 218 days.

This patent is subject to a terminal disclaimer.

(21) Appl. No.: 15/919,803

(22) Filed: Mar. 13, 2018

(65) Prior Publication Data

US 2018/0204181 A1 Jul. 19, 2018

Related U.S. Application Data

(63) Continuation of application No. 13/488,759, filed on Jun. 5, 2012, now Pat. No. 9,946,991.

(60) Provisional application No. 61/503,156, filed on Jun. 30, 2011.

(51) Int. Cl.
*G16H 15/00* (2018.01)
*G06Q 10/10* (2012.01)

(52) U.S. Cl.
CPC ............. *G06Q 10/10* (2013.01); *G16H 15/00* (2018.01)

(58) Field of Classification Search
CPC .... G06Q 50/22; G06Q 10/10; G06F 16/2455; G06F 16/955; G16H 15/00

USPC ............................................................ 705/2
See application file for complete search history.

(56) References Cited

U.S. PATENT DOCUMENTS

| | | | |
|---|---|---|---|
| 4,733,354 A | 3/1988 | Potter et al. | |
| 6,564,213 B1 | 5/2003 | Ortega | |
| 7,657,396 B1 | 2/2010 | Brown et al. | |
| 8,099,722 B2 | 1/2012 | Fairweather | |
| 2006/0136259 A1 | 6/2006 | Weiner et al. | |
| 2007/0233644 A1* | 10/2007 | Bakalash | G06F 16/2455 |
| 2008/0071757 A1* | 3/2008 | Ichiriu | G06F 16/951 |
| 2010/0057645 A1 | 3/2010 | Lauritsen | |
| 2011/0066425 A1 | 3/2011 | Hudgins et al. | |

* cited by examiner

*Primary Examiner* — Hiep V Nguyen
(74) *Attorney, Agent, or Firm* — Jonathan L. Tolstedt

(57) ABSTRACT

Medical coding systems receive as input medical terms which coders classify into medical codes, used in the remuneration of medical procedures. A set of applicable medical codes can be determined by intersecting multidimensional data structures associated with the input terms and counting medical codes occupying regions of intersection. If the resulting set contains a single code, it is presented to the coder for verification. If the resulting set contains more than a single code, the coder can be questioned in a variety of ways to access, and select from, terminology options not implied by the originally provided input terms. The interactive process may also use the multidimensional data structures to regulate the order of questions, present decision aids, and select related procedure codes. The interaction concludes when the coder has fully specified the proper code or codes that describe the required procedure or procedures.

20 Claims, 14 Drawing Sheets

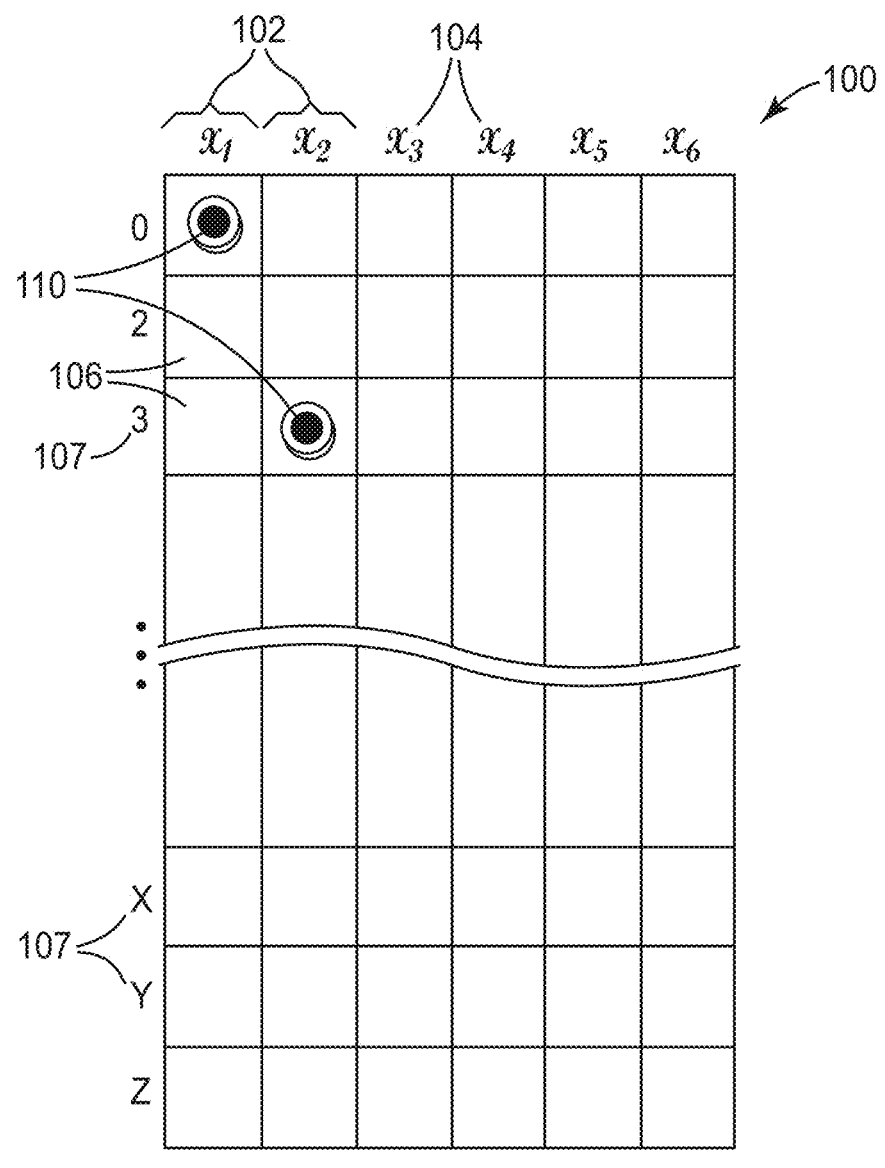
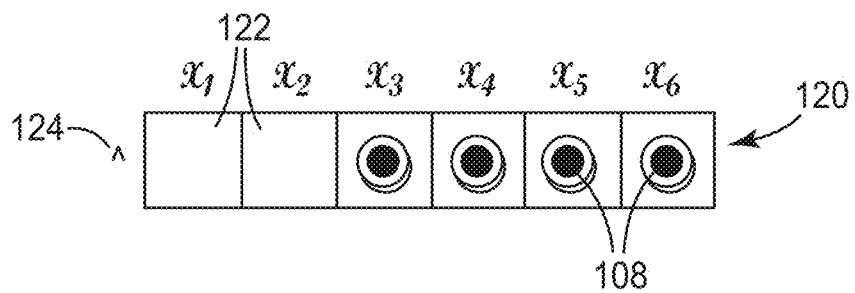
FIG. 2

← 260

Terms: excision lesion bra

*excision lesion* brachialis muscle
*excision lesion* brachial artery
*excision lesion* brachial lymph node
*excision lesion* brachial plexus
*excision lesion* brachial vein
*excision lesion* brachiocephalic artery
*excision lesion* brachiocephalic trunk
*excision lesion* brachiocephalic vein
*excision lesion* brachioradialis muscle
*excision lesion* brain
(back up)

00BC0ZZ Excision of Cerebellum, Open Approach

| | | |
|---|---|---|
| Accept | Revise | Copy | Remove |

*Medical and Surgical* — 0 Medical and Surgical

*Body System* — 0 Central Nervous System

*Operation* — B Excision: Cutting out or off, without replacement, a portion of a body part

| *Body Part* | *Approach* | *Device* | *Qualifier* |
|---|---|---|---|
| 0 Brain | | | |
| 1 Cerebral Meninges | | | |
| 2 Dura Mater | | | |
| 6 Cerebral Ventricle | | | |
| 7 Cerebral Hemisphere | | | |
| 8 Basal Ganglia | | | |
| 9 Thalamus | | | |
| A Hypothalamus | | | |
| B Pons | | | |
| C Cerebellum | 0 Open | Z No Device | X Diagnostic |
| D Medulla Oblongata | 3 Percutaneous | | Z No Qualifier |
| F Olfactory Nerve | 4 Percutaneous Endoscopic | | |
| G Optic Nerve | | | |
| H Oculomotor Nerve | | | |
| J Trochlear Nerve | | | |
| K Trigeminal Nerve | | | |

*FIG. 9*

```
01  b
02   a
03    ck [405]
04     ~
05      fascia [406]
06      s
07       kin [407]
08           radiation oncology [408]
09        ubcutaneous tissue [409]
10     ffle repair atrial septum [410]
11     l
12      anoplasty [411]
13      loon
14          angioplasty [412]
15          pump intra-aortic [413]
16     nd
17      age [414]
18       ~
19          change [5839]
20          dressing [5840]
21          removal [5841]
22        , elastic [416]
23      ing [417]
24       ~
25          artery [418]
26          gastric [419]
27          laparoscopic gastric [420]
28          pulmonary artery [421]
29     r
30      ium swallow [422]
31      tholin's gland [423]
32     s
33      al
34          cerebral vein [424]
35          ganglia [425]
```

```
carbon 11
carbon 11 nuclear medicine
cardia
cardiac
cardiac cath
cardiac catheterization
cardiac imaging
cardiac lead
cardiac mapping
cardiac massage, external
cardiac massage, open
cardiac nerve
cardiac pacemaker removal
cardiac plexus
cardiac resynchronization defibrillator pulse generator
cardiac resynchronization pacemaker pulse generator
cardiac rhythm related device
```

*FIG. 16*

```
excision cardia
excision cardiac nerve
excision cardiac plexus
excision cardioesophageal junction
excision carina
excision caroticotympanic artery
excision carotid artery
excision carotid body
excision carotid glomus
excision carotid sinus
excision carotid sinus nerve
excision carpal
excision carpal joint
excision carpal tunnel
excision carpectomy
excision carpometacarpal joint
excision carpometacarpal ligament
excision cartilage, ear
excision cartilage, joint
excision cartilage, nose
```

*FIG. 17*

METHODS USING MULTI-DIMENSIONAL REPRESENTATIONS OF MEDICAL CODES

CROSS-REFERENCE TO RELATED APPLICATION DATA

This application claims the benefit of U.S. Provisional Application Ser. No. 61/503,156, filed Jun. 30, 2011.

1. FIELD OF THE INVENTION

Computer-implemented methods are provided to assist in medical coding. More particularly, computer-implemented methods are provided to facilitate specification of medical procedure codes.

2. DESCRIPTION OF THE RELATED ART

Medical coding is a process used to classify medical care. The codes so created are frequently used in the U.S. to reimburse a healthcare organization by a suitable payment organization for services provided to a patient. This process generally involves transforming narrative descriptions of diseases, injuries, and/or other healthcare procedures into standardized alphanumeric designations, called medical codes. These codes are sufficiently detailed to accurately describe the diagnosis (i.e. what is wrong with the patient) and procedures performed to test or correct these diagnoses. Once the codes are determined, they are generally submitted in a payment request to the payment organization, which then reviews the codes and makes a payment.

The International Classification of Diseases, 10th Edition, Procedure Coding System (ICD-10-PCS) is an American system of medical classification used for inpatient procedure codes. The U.S. Department of Health and Human Services has mandated use of this coding system to be used for reporting inpatient surgical procedures on HIPAA (Health Insurance Portability and Accountability Act) hospital claims beginning in 2013. This requirement has given rise to a demand for computer-based tools to assist hospitals for efficiently and accurately reporting their procedures.

As procedures are performed on a patient in the hospital, detailed narrative accounts are produced (often by dictation and transcription or direct entry into Electronic Health Records). These accounts, sometimes called operative reports, are part of the patient's permanent medical record. During the patient's stay, or after discharge, the narratives can be read either by computer programs called "autocoders" or by trained medical records technicians called "medical coders." When medical coders perform these tasks, they are often assisted by other computer programs called "encoders." The overall process transforms the narration into one or several procedure codes, which abstract the procedures performed during the patient's stay according to the rules of the target coding system, published guidelines, and generally accepted professional coding practice.

3. SUMMARY OF THE INVENTION

Provided herein are computer-implemented medical coding methods that use multi-dimensional data structures to implement a target coding system such as ICD-10-PCS. These methods can be used in computer programs such as autocoders and encoders, and provide several enhancements over existing medical coding products. For example, the coding method can provide, in a user interface, an updated list of valid terminology options for each character of the ICD-10-PCS procedure code at each step of the coding process. The coder can select amongst these terminology options to quickly and efficiently arrive at the targeted procedure code. Refreshing the valid terminology options at each coding step is particularly advantageous where the terminology options associated with one code character depends, in part, on the selection of one or more terminology options for a different code character. The same user interface can also show the partially or fully unpopulated procedure code, along with the total number of codes associated with the presently defined procedure code, as the existing set of terminology options is progressively revised by the medical coder.

These coding methods also provide great versatility in allowing for "backing up" in the event the medical coder changes his or her mind as to a previously selected terminology option. Using conventional tree-based coding schemes, a medical coder is generally constrained to operate along a particular coding path, based on the order in which the code characters are specified. The provided coding methods, on the other hand, allow the medical coder to "take back" one or more previously specified terminology options along a different coding path than that previously used. The medical coder can also specify terminology options by direct selection in the user interface or by entering one or more input terms that are processed using a dictionary that correlates known input terms and known terminology options to each other.

In one aspect, a method is provided for facilitating, through a medical coder, the specification of an n-character ICD-10-PCS procedure code. The method comprises: for at least some of the n characters, presenting in a graphical user interface one or more valid terminology options associated with each respective character; receiving, from the medical coder, selection input associated with one or more of the valid terminology options; and in response to receiving the selection input from the medical coder, updating the user interface to present revised valid terminology options associated with one of the n-characters for which there has been no selection input.

In another aspect, a method is provided for refining, through a medical coder, the specification of an n-character ICD-10-PCS procedure code, comprising: providing, in a graphical user interface, valid terminology options, each associated with one of the n characters; receiving from the medical coder a plurality of selection inputs, each associated with at least one of the valid terminology options, to progressively revise the terminology options while updating the user interface to present revised terminology options after each selection input; and receiving additional input from the medical coder to correct a previously received selection input other than the most recently received selection input to determine corrected terminology options.

In still another aspect, a method is provided for facilitating, though a medical coder, the complete specification of a partially populated n-character ICD-10-PCS procedure code having at least one unpopulated character and at least one populated character, comprising: calculating, based on the populated character or characters, valid values associated with the at least one unpopulated character; presenting to the medical coder, via a graphical user interface, valid terminology options associated with the valid values; receiving selection input from the medical coder specifying the selection of a terminology option presented; and based on the selection input, associating a valid value with the at least one unpopulated character.

In still another aspect, a non-transitory computer-readable medium is provided for facilitating, through a medical coder, specification of an n-character ICD-10-PCS procedure code. The computer-readable medium comprises instructions operable to cause a computer to: for at least some of the n characters, generate in a graphical user interface two or more valid terminology options associated with each respective character; receive, from the medical coder, selection input associated with one or more of the valid terminology options; and in response to receiving the selection input from the medical coder, update the user interface to present revised valid terminology options associated with one of the n-characters for which there has been no selection input.

In still another aspect, a non-transitory computer-readable medium is provided for facilitating, through a medical coder, specification of an n-character ICD-10-PCS procedure code, the computer-readable medium comprising instructions operable to cause a computer to: provide, in a graphical user interface, valid terminology options, each associated with one of the n characters; receive from the medical coder a plurality of selection inputs, each associated with at least one of the valid terminology options, to progressively revise the terminology options while updating the user interface to present revised terminology options after each selection input; and receive additional input from the medical coder to correct a previously received selection input other than the most recently received selection input to determine corrected terminology options.

In still another aspect, a non-transitory computer-readable medium is provided for facilitating, though a medical coder, the complete specification of a partially populated n-character ICD-10-PCS procedure code, the computer-readable storage medium comprising executable instructions operable to cause a computer to: calculate, based on the populated character or characters, valid values associated with the at least one unpopulated character; present to the medical coder, via a graphical user interface, valid terminology options associated with the valid values; receive selection input from the medical coder specifying the selection of a terminology option presented; and based on the selection input, associate a valid value with the at least one unpopulated character.

In still another aspect, a user interface is provided for facilitating, through a medical coder, the specification of an n-character ICD-10-PCS procedure code. The user interface comprises: a first pane presenting a partially unpopulated seven-character ICD-10-PCS code having a plurality of unpopulated characters; and a second pane providing, for each unpopulated character, two or more valid terminology options associated therewith, each terminology option being selectable by the medical coder to progressively populate the procedure code.

In still another aspect, a computer-based system is provided for facilitating, from a medical coder, the specification of an n-character ICD-10-PCS code. The computer-based system comprises: an encoder module operable to present to the medical coder a plurality of valid terminology options associated with at least some of the n characters, then to receive from the medical coder selection input associated with the presented valid terminology options; a hyperslice dictionary interpreter module operable to receive, from the user encoder module, the selection input and based thereon, determine revised valid terminology options for characters for which there has been no selection input.

These concepts provide a new relationship based model to perform PCS coding instead of a conventional static based hierarchical models. This relationship based model can provide an enhanced user experience that involves dynamically navigating through ICD-10 PCS coding using table-based navigation, leading to a more versatile and efficient coding process.

4. BRIEF DESCRIPTION OF THE DRAWINGS

FIG. 2 is a diagram showing a data structure representing medical codes in a multi-dimensional abstract space.

FIGS. 4-6 are partial screenshots showing a search being performed in the system.

FIGS. 7-8 are partial screenshots showing search results in the system.

FIG. 9 is a partial screenshot of a confirmation screen in the system.

FIG. 10 is diagram showing a tree representation used in an implementation of the system.

FIGS. 13-15 are partial screenshots showing user queries in the system.

FIGS. 16-17 are partial screenshots showing an implementation of the data structure in FIG. 2 in a search being performed in the system.

5. DETAILED DESCRIPTION OF THE ILLUSTRATIVE EMBODIMENTS

Figure 1:
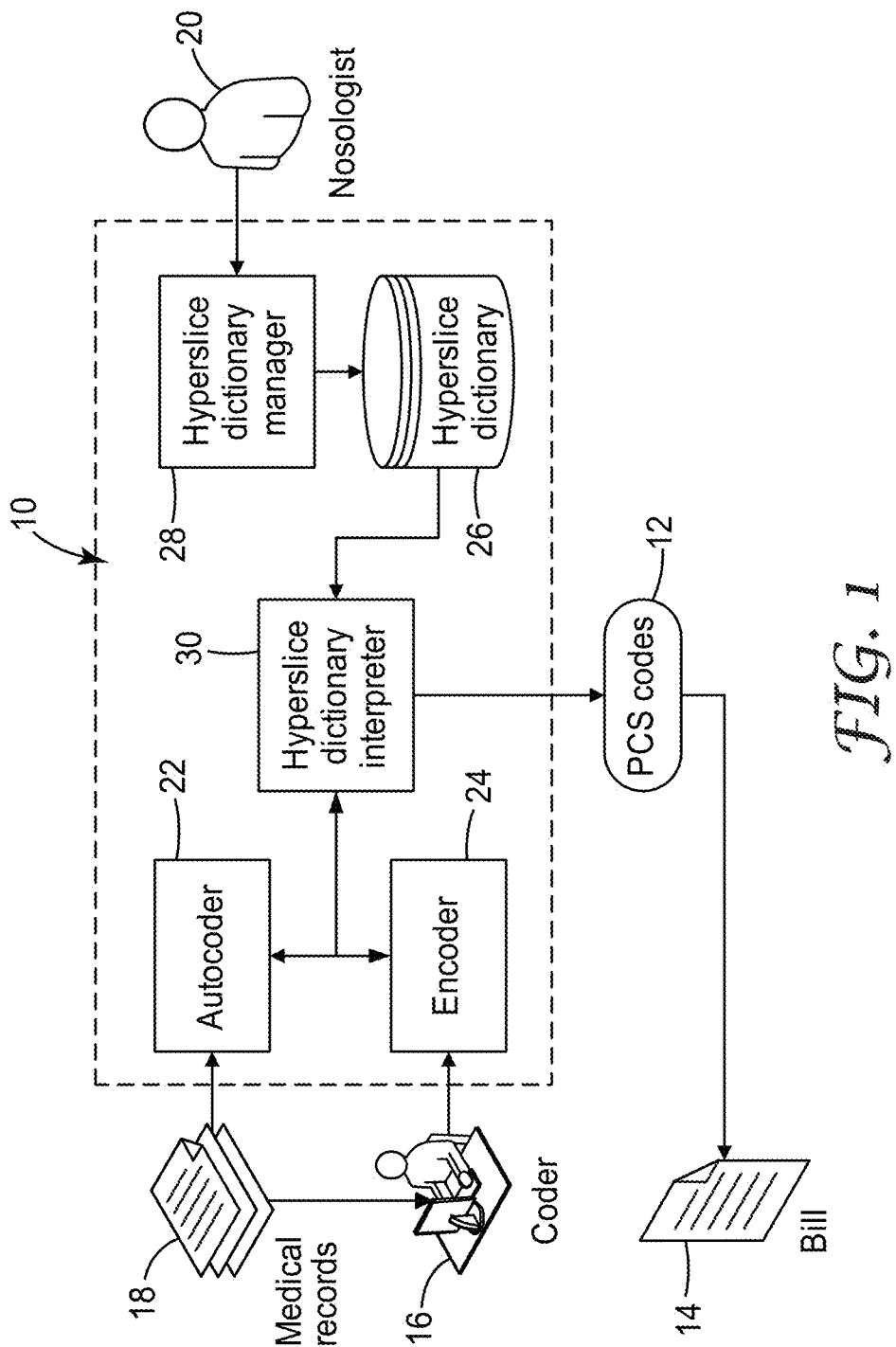
FIG. 1 is a diagram showing systems that can be used by a healthcare organization, including one embodiment of a medical encoder system.

Described herein are exemplary embodiments, shown with reference to the accompanying drawings. This invention may be embodied in many different forms and should not be construed as limited to the embodiments set forth herein; rather, these embodiments are provided so that this disclosure will be thorough and complete, and will fully convey the scope of the invention to those skilled in the art.
ICD-10-PCS Code Structure Each ICD-10-PCS code consists of seven characters. Each character may be a numeral (0-9) or a capital unaccented Roman letter (A-Z), with the exception of the letters "I" and "O," which are deemed too easily confused with the characters "1" and "0." The set of possible character values (i.e. 0, 1, 2, 3, 4, 5, 6, 7, 8, 9, A, B, C, D, E, F, G, H, J, K, L, M, N, P, Q, R, S, T, U, V, W, X, Y, and Z) is commonly known as the "PCS character set." Each of the seven character positions may contain one of the 34 possible values in the PCS character set, yielding a theoretical possibility of 34', or roughly 52 billion codes. Only 72,081 codes are used in the 2011 version. New codes are added on an annual basis by the HHS Centers for Medicare and Medicaid Services (CMS).

It was discovered that these seven-character codes can be conveniently represented on a computer using specialized, multi-dimensional data structures capable of representing one or more codes. These data structures are referred to herein as "hyperslices." A hyperslice could represent, for example, a single valid ICD-10-PCS code such as "0FB00ZX." Here, each character value in the sequence "0", "F", "B" "0", "0", "Z", and "X" is associated with a given dimension in a pre-defined multidimensional abstract space.

As another example, a hyperslice could also represent more than one valid code, through the use of ranges and wildcards. Conversely, since the abstract space is only sparsely populated with valid codes, it is also possible to create hyperslices that represent zero valid codes. Further options and advantages of hyperslices will be described in detail in later sections.

In this medical coding system, each of the seven character positions has a defined meaning, independent of the values found in the other positions, with one exception. The first position of each code is called the "Section" and in the 2011 version has one of the following sixteen values provided in Table 1, below.

TABLE 1

Section values and respective definitions

| | |
|---|---|
| 0 | Medical and Surgical |
| 1 | Obstetrics |
| 2 | Placement |
| 3 | Administration |
| 4 | Measurement and Monitoring |
| 5 | Extracorporeal Assistance and Performance |
| 6 | Extracorporeal Therapies |
| 7 | Osteopathic |
| 8 | Other Procedures |
| 9 | Chiropractic |
| B | Imaging |
| C | Nuclear Medicine |
| D | Radiation Oncology |
| F | Physical Rehabilitation and Diagnostic Audiology |
| G | Mental Health |
| H | Substance Abuse Treatment |

A character position in PCS is called an "axis of classification." Here, the Section determines a meaning for each of the remaining six axes of classification. The vast majority of procedural codes begin with "0," which yields the set of definitions shown in Table 2, below.

TABLE 2

Axes of classification and respective definitions

| | |
|---|---|
| 1 | Section 0 = Medical/surgical |
| 2 | Body System |
| 3 | Operation |
| 4 | Body Part |

TABLE 2-continued

Axes of classification and respective definitions

| | |
|---|---|
| 5 | Approach |
| 6 | Device |
| 7 | Qualifier |

Here, as long the first axis is set "0," the definitions of remaining axes (2-7) remain fixed. For example, the sixth axis stands for the Device involved in the procedure, assuming one exists. If no device is used, the character associated with the sixth axis is assigned the value "Z." All seven characters are filled in for a valid procedure code. Other sections may have different definitions for their axes of classification, but again the definitions are fixed once the Section has been determined.

The definitions of the 34 possible values in the remaining six axes of classification sometimes depend on the values for other axes of classification. For example, in the Medical and Surgical section, the meaning of "0" in the sixth axis is always "Drainage Device." However, the meaning of "0" in the fourth axis (Body Part) depends on which value has been used in the second axis (Body System). Because there are far more than 34 body parts identified in PCS, the definition of the values in the Body Part axis depend on the values in Body System axis. For example, in section 0, if the Body System is "0" (Central Nervous System) then a "6" in the fourth axis means "Cerebral Ventricle." But if the Body System is "2" (Heart and Great Vessels) then a "6" in the fourth axis means "Right Atrium."

Where possible, PCS is generally consistent with axes of classification which require fewer than 34 values across all codes in a section. For example, there are only seven different values for Approach (axis 5) in all of Section 0, so all 62,000+ codes in that Section apply the same meanings to the seven values.

The official list of defined PCS codes and the meaning of the values in their axes of classification is published annually by CMS on their official internet website. The publication represents the defined codes in a series of tables. An exemplary table of published PCS codes, and their respective meanings, is shown in Table 3, below. For each valid combination of values in the first three axes of classification (Section, Body System, and Operation), subsequent rows of the table give combinations of valid values for the other four axes (Body Part, Approach, Device, and Qualifier).

TABLE 3

Exemplary table of published PCS codes

| | |
|---|---|
| Section | 0 Medical and Surgical |
| Body System | F Hepatobiliary System and Pancreas |
| Operation | B Excision: Cutting out of off, without replacement, a portion of a body part |

| Body Part | Approach | Device | Qualifier |
|---|---|---|---|
| 0 Liver | 0 Open | Z No device | X Diagnostic |
| 1 Liver, Right Lobe | 3 Percutaneous | | Z No Qualifier |
| 2 Liver, Left Lobe | 4 Percutaneous Endoscopic | | |
| 4 Gallbladder | | | |
| G Pancreas | | | |
| 5 Hepatic Duct, right | 0 Open | Z No device | X Diagnostic |
| 6 Hepactic Duct, Left | 3 Percutaneous | | Z No Qualifier |

TABLE 3-continued

Exemplary table of published PCS codes

| | |
|---|---|
| 8 Cystic Duct | 4 Percutaneous Endoscopic |
| 9 Common Bile Duct | 7 Via Natural or Artificial Opening |
| C Ampulla of Vater | 8 Via Natural or Artificial Opening Endoscopic |
| D Pancreatic Duct | |
| F Pancreatic Duct, Accessory | |

Under PCS, the descriptors used in an axis of classification are carefully selected and have precise definitions. Under ICD-10-PCS, the "-ectomies" and "-otomies" previously used under ICD-9-PCS and CPT are replaced by a set of root operations, each having its own independent definition. This change can provide both benefits and challenges. The benefits flow from the precise, constant and verifiable nature of PCS codes, leading to greater analytical precision for records whose procedures are coded in PCS. As a further advantage, once coders become accustomed to using PCS terms, manual coding of procedures is expected to be faster, more consistent and more reliable.

One challenge addressed by the provided coding methods is connecting PCS and current modes of expression (namely dictated, written and electronic). Difficulties arise when these modes of expression use current medical terminology not used in PCS, or alternatively use PCS terms in variable and imprecise ways. "Angioplasty" for example, is not used anywhere in PCS, and must therefore be connected with the PCS term that defines the correct procedural objective. For example, while "excision" is used in current medical terminology to encompass several procedural objectives, "excision" as defined in PCS means only one procedural objective.

Workflow Overview

FIG. 1 shows exemplary components that can be used in a medical coding system 10 for a healthcare organization. As shown, the system 10 facilitates the process of representing a patient's encounter with a healthcare organization by providing one or more PCS codes 12, which can then be submitted as a bill 14 to a payment organization (e.g. an insurance company or the government) for review and payment. The system 10 includes various interfaces for interacting with medical records 18, a medical coder 16, and/or a nosologist 20. Optionally, the system 10 can be incorporated into one of any number of commercially available coding systems. One such coding system is that which is marketed by 3M Health Information Systems of Salt Lake City, Utah under the trade name "3M Coding & Reimbursement System."

The graphical user interfaces used by the system 10 where coder 16 can access and enter codes that define aspects of a patient's encounter with the healthcare organization can take different forms. In various embodiments, the healthcare organization coding system may support a plurality of such interfaces, both web-based and locally hosted.

As further shown in FIG. 1, the system 10 includes component parts or software-based modules that interact with each other during the coding process. As medical procedures are performed on a patient in the healthcare organization, detailed narrative accounts are generally produced by the treating physician. These accounts can be produced by dictation and transcription or by direct entry into the Electronic Health Records. In any case, these accounts can become part of the patient's permanent medical records 18. In some embodiments, the narratives are directly read by computer programs called autocoders 22. Alternatively, the narratives can be read by coders 16 with the assistance of computer programs, or modules, called encoders 24. Encoders also present a graphical user interface to the coder to facilitate the coding activity, by receiving input from the coder. The system 10 can interact with a user using a client computer, which generally includes a processor, input device, memory, and display device.

In exemplary embodiments described herein, the system 10 uses hyperslices to represent medical codes. As mentioned earlier, these hyperslices define regions of multidimensional point space. When used to implement the ICD-10-PCS coding system, each dimension preferably corresponds to one, and only one, axis of classification in an ICD-10-PCS procedure code.

Hyperslices can be associated with terminology options, which represent medical procedure concepts. This association can be implemented through computer analysis of the published definitions of PCS and accompanied by review, correction and extension by nosologists. In the system 10, terminology options can be articulated and/or identified using input terms (such as words or phrases in some language) used for recording inpatient procedure details in medical records. These input terms can include, for example, concept identifiers in the Electronic Health Records.

Referring again to FIG. 1, input term-hyperslice relationships can be stored in a hyperslice dictionary 26 using representations that allow rapid recognition of terms and fast manipulation of hyperslices. The hyperslice dictionary 26 can be conveniently edited by the nosologist 20 using a hyperslice dictionary manager 28. The hyperslice dictionary 26 can also be accessed by the autocoder 22 or encoder 24 through a hyperslice dictionary interpreter 30.

The hyperslice dictionary interpreter 30 may receive selection input from the coder 16, as facilitated via the encoder 24, and based on this input determine valid selection inputs that representing terminology options associated with characters in the PCS codes for which no selection input has been received. It is possible that the valid selection inputs associated with various characters in the PCS codes may change, based on which characters have been specified (or selected) by the coder 16. The hyperslice dictionary interpreter 30 may then provide indicia of these newly determined valid selection inputs for remaining characters in the PCS code, and provide these to the encoder 24. The encoder 24 then may update the graphical user interface with which the coder 16 is interacting to show the updated valid terminology options for those PCS characters that have not yet been specified. This process, and interaction, between the coder 16, the encoder 24, and hyperslice dictionary interpreter 30 iteratively proceeds, progressively closing in on a final, valid PCS code.

When the coder 16 provides input terms to describe a particular medical procedure, the system 10 can drive intelligent look-ahead processes to help the coder 16 see what terms are available in context. Any set of recognized terms can be combined by intersecting their associated hyperslices and counting the PCS codes 12 occupying the regions of six-dimensional space thus defined. If the resulting set contains just one code, the set can be presented to the coder 16 for verification. If the resulting set contains more than one code, the coder 16 (or autocoder 22) may be questioned in a variety of ways to obtain the choices not implied by the originally provided terms.

In sum, this method can transform the initial narration into one or several PCS codes 12 that abstract the procedures performed on the patient according to rules of the target coding system, published guidelines, and generally accepted professional coding practice. In preferred embodiments, the interactive process uses hyperslices to regulate the order of questions, the presentation of decision aids, the selection of related procedure codes, and other decisions. The interaction may conclude when the coder 16 has determined a complete set of PCS codes 12 that describes the procedure or procedures required on the hospital discharge abstract.

Defining Hyperslice Regions

Because the meanings of the axes of classification are fixed by the value of the first character representing the Section, each of the sixteen Sections in the PCS coding system can be represented by its own six-dimensional point space. In a preferred embodiment, each dimension corresponds to an axis of classification and consists of 34 values, arrayed alphanumerically (0-9, A-H, J-N, P-Z). Each point in this abstract space is a potential PCS code. This space can be referred to as a PCS-n-section space, where n is one of the 16 valid Section values. The vast majority of the 1.5 billion potential codes in a given PCS-n-section space are unused, so the defined PCS codes constitute a sparse point set in the space.

In this embodiment, a given region within a PCS-n-section space of the cross product of independently defined value sets for each of the six dimensions. In other words, a region defines a set of values for each axis of classification, and the "rectangular" region consists of all points in the space whose values in the respective axes of classification are in the sets. For example, the first three rows of the table above define a hyperslice region as follows:

Axis 1=value 0
Axis 2=value F
Axis 3=value B
Axis 4=values 0 or 1 or 2 or 4 or G
Axis 5=values 0 or 3 or 4
Axis 6=value Z
Axis 7=value X or Z There are 30 points (1×1×5×3×1×2) in this region of PCS-0-section space. Since this region was defined from the PCS definition, every one of the 30 points represents a valid PCS code. However, this need not be the case. For example, consider the following rectangular region, defined the same as above, but with Axes 6 and 7 restricted to only digit values:

Axis 1=value 0
Axis 2=value F
Axis 3=value B
Axis 4=values 0 or 1 or 2 or 4 or G
Axis 5=values 0 or 3 or 4
Axis 6=values 0 . . . 9
Axis 7=values 0 . . . 9

This region has 1,500 points though none of them are currently in use as valid PCS codes. It is common to define regions where one or more axes are not restricted, i.e. can take on any of PCS's 34 allowed values. Another region may be defined as follows:

Axis 1=value 0
Axis 2=value F
Axis 3=value B
Axis 4=any PCS character
Axis 5=any PCS character
Axis 6=any PCS character
Axis 7=any PCS character This is a region of PCS-0-section space with 1,336,336 points but only 100 codes (namely those defined by Table 3, above). As used herein, a "slice" is a region defined when one or more of the axes of classification are unrestricted. This may produce, for example, a lower-dimensional subspace in the same way that a plane is a lower dimensional subspace of three-dimensional Euclidean space. A hyperslice can thus be thought of as a "slice" taken through, for example, a six-dimensional PCS-n-section space. When slices are intersected, these intersections can produce lower-dimensionality slices or regions, so the term has been extended to include the products of slice intersection.

Hyperslice Notation and Representation

Hyperslice notation can be used to facilitate communication between a user and the system 10. As used herein, a hyperslice specification is a string of characters. In an exemplary embodiment, there are seven character specifications in the string, corresponding to seven concatenated axis specifications. For simplicity, a given axis specification can be limited to one of the following three types:

1) a single PCS character, indicating that the axis is limited to points with that character value
2) a list of PCS characters enclosed in square brackets (for example, [13456BZ]). Optionally, commas may be used for readability but these are otherwise ignored. As a further option, a dash may be used to include all of the PCS characters between the characters specified. For example, [13456BZ] could also be expressed as [1,3-6,B,Z]. The characters need not be listed in order.
3) a caret ("^"), to indicate any PCS character. Alternatively, a star ("*") or question mark ("?") could also be used.

Under this system, the notation 0G3[2-4HN-R]^^Z denotes the following hyperslice:

Axis 1=value 0
Axis 2=value G
Axis 3=value 3
Axis 4=values 2 or 3 or 4 or H or N or P or Q or R
Axis 5=any PCS character
Axis 6=any PCS character
Axis 7=value Z To the extent that this notation is used to represent ICD-10 codes, the first character (i.e. the Section) is preferably defined with a single value. While the above notation scheme allows the first character to be a choice—for example, [01]^^^4^Z—such expressions are not preferred because the meanings of the remaining axes of classification may not be consistent. The system 10, encountering the above hyperslice, could either translate it into 0^^^^4^Z or treat it as an error.

FIG. 2 illustrates portions of an exemplary data structure that may be used to represent a defined hyperslice region. It can be advantageous to use a space-efficient representation that allows efficient mathematical manipulation of hyperslices. In this embodiment, a hyperslice region is represented as a three-part data structure:

1) An array 100 of bit strings 102, one for each of six axes of classification 104. Each bit string 102 consists of thirty-four bits 106, with each bit 106 corresponding to a pre-defined PCS character value 107. The bits that are "on" (shown here by markers 110) indicate individual character values 107 allowed in the hyperslice.

2) A bit string 120 of bits 122, again one for each axis of classification 104. The bit is on if and only if the caret 124 (which represents all PCS characters) is specified for the axis of classification 104. In this example, the caret 124 is specified for axes of classification 104 denoted by $x_3$, $x_4$, $x_5$, and $x_6$.

3) An integer counting the number of valid PCS codes (occupied points) in the slice (not shown in FIG. 2).

If desired, one or both of parts 2) and 3) can be omitted. If part 2) is omitted, for example, the caret 124 could be alternatively represented by turning on all thirty-four bits 106 in the corresponding bit string 102 of the array 100.

When the valid PCS code count is unknown, it can be set to some pre-defined value such as 999,999. This value is much greater than the total number of valid PCS codes ever expected to be used. This is called the uncounted flag, and a hyperslice with the uncounted flag in its count field is referred to as an "uncounted hyperslice." Note that a count of zero is a valid count, as it is common for a hyperslice to not contain any valid codes.

In some embodiments, the count is set to a negative number to indicate that the hyperslice itself is invalid for some reason. This may occur, for example, if it were created by an invalid hyperslice specification or if a processing error occurred in the system 10. A hyperslice with a negative code count is referred to as an "error hyperslice." In an object-oriented language such as C# or Java, the structure defined above could be a "hyperslice class" and the routines to be described below could be methods of the class.

Primitive Hyperslice Routines

The system 10 can use primitive routines to facilitate manipulation of these hyperslices. For example, these routines could include a hyperslice parser, hyperslice printer, and a hyperslice intersector.

A hyperslice parser accepts a character string as input, the character string allegedly containing a hyperslice specification. The output is a hyperslice representation. The parser functions by reading the input character string from left to right and populating the hyperslice representation with what it finds. This reading process can be executed using common techniques known in the art. If the hyperslice specification is well-formed, then the hyperslice is returned with the count field set to the uncounted flag. If not, then a negative count can be recorded indicating the type of error discovered and the rest of the hyperslice representation can be left undefined. Optionally, this routine is created using an object oriented language and is embedded in, for example, a hyperslice constructor.

A hyperslice printer accepts a hyperslice representation as input. The output is a character string containing a hyperslice specification. The bits in the hyperslice representation can be interrogated to construct, for example, a canonical string representation of the hyperslice. In a language that supports the construct, for example, the printer can be treated as an override of the toString( ) method.

A hyperslice intersector accepts as input two hyperslice representations that are in the same Section (i.e. having the same value for the first character of the ICD-10-PCS code). The output is a hyperslice that represents the intersection in PCS-n-section space of the two input hyperslices. In preferred embodiments, a Boolean "and" operation is executed for the corresponding bit strings of the two hyperslices and the result is used to populate the output hyperslice. The count field of the hyperslice is set to the uncounted flag unless any one of the axes is empty, meaning that all bits in the corresponding bit string are off. In this case, there are necessarily no valid codes in the region and the count field is simply set to zero.

Computing the Hyperslice Code Count

Whether it is formed from a hyperslice specification directly, or formed from the intersection of two existing hyperslices, a new hyperslice generally starts with a code count set to the uncounted flag. Preferably, the system 10 is capable of conveying to the medical coder how many codes are included in a given hyperslice. This can be accomplished using a hyperslice code counter. This program takes a hyperslice representation as input and produces an output hyperslice representation whose code count field contains the number of current ICD-10-PCS codes occupying points in its PCS-n-section space. In some cases, this number is zero. The output hyperslice representation contains only those axis values actually found to be occupied by a valid ICD-10-PCS code.

Notably, the output hyperslice representation can still identify more points than codes. For example, if the codes 00B40ZZ and 00B50ZZ are valid codes, but 00C40ZZ and 00C50ZZ are not, then the hyperslice 00[BC][45] discovered by this process would identify four points but only two valid codes.

The computation is facilitated by a PCS code Definition Database (PCDD) that is derived from the official PCS documents posted on the CMS website. The PCDD contains the following tables:

PCS Code Table. This lists every currently valid code along with dependencies, if any, between its axes of classification. In other words, if one axis of classification in the code depends on another for the meaning of its values, that dependency is represented in this table.

PCS Label Table. For each Section and Axis of classification, this table lists the meaning of each character value in use for the axis and the dependencies, if any, with character values in other axes.

PCS Header Table. For each Section and Axis of classification, this table lists the meaning of each Axis.

PCS Index Table. This table provides PCS index entries and their associated PCS code references.

PCS Reference Table. This table provides entries in the PCS reference section of the CMS documentation. For example, this could include the body part key and associated ICD-10-PCS code references.

To count the codes in a given hyperslice, the hyperslice code counter uses the hyperslice representation to derive the lowest and highest possible ICD-10-PCS code that may be included in the hyperslice. In a preferred embodiment, the following steps are executed:

1) The PCS code table is entered at the lowest point.
2) Each code is transformed into an array of seven bit indices.
3) The code bit indices are tested against the hyperslice bit array. If all axes come up with a match, then the code is counted.
4) The process terminates when the highest point has been reached.

Advantageously, a PCS code table consisting of about 72,000 codes of seven characters each only requires about 500K of memory. This small amount of information can be easily cached, making the above process very fast.

Associating Hyperslices with Clinical Terminology Options

Hyperslices are particularly advantageous because they can be associated with terminology options representing standardized clinical or anatomical concepts in the medical coding art. These in turn can be associated with terms that might be present in the medical record which represent those terminology options. Exemplary terminology option/hyperslice associations are shown in Table 2, below:

TABLE 2

Terminology option/hyperslice associations

| Terminology option | Hyperslice |
|---|---|
| Achillotenotomy | 0L[89][NP]^^Z |
| Back | 0W^[KL]^^^ |
| Bandage | 2^^^^4^ |
| Clavicle | 0P^[9B]^^^ |
| Decompression laminectomy | 0[RS]B^^Z |
| Excision | 0^B^^^^ |
| Internal fixation device | 0[NPQRS]^^^4^ |
| Laparoscopic | 4 slices, 2 in Section 0: 0W^[GHJPR]4^^and 0[DTFU]^^4^^ |
| Left | 51 slices such as 0[UXY]^1^^^ |
| Left clavicle | 0P^B^^^ |
| Leg | 4 slices, 2 in Section 0: 0Y[CDHJ]^^^and 0[JL]^[LMNP]^^^ |
| Percutaneous | [01348]^^^3^^ |
| Percutaneous transluminal coronary angioplasty | 027[0123]3[4DTZ]^ |
| PTCA | 027[0123]3[4DTZ]^ |
| SNOMED-CT CID 11101003 | 027[0123]3[4DTZ]^ |
| Sacroiliac ligament | 0M^[CD]^^^ |

A hyperslice can represent a terminology option expressible in PCS terminology independently of the terms used to express the same outside of PCS. For example, in the hyperslice associations shown above, "Percutaneous transluminal coronary angioplasty," "PTCA," and "SNOMED-CT concept ID 11101003" are all equivalent ways of expressing the same terminology option, and hence are associated with the same PCS hyperslice.

A given terminology option may also require more than one hyperslice to represent all the ways it is used in PCS. As an extreme example, "left" by itself requires 51 different hyperslices to represent all the places that laterality—that is, "left" or "right"— appears in PCS coding.

In some embodiments it may be more efficient to create hyperslices that are subsets of other hyperslices. For example, "clavicle," with hyperslice 0P^[9B]^^^ could be combined with "left," with its 51 hyperslices (of which 0^^B^^^ is a member) and the combination would yield 0P^B^^^(using a process to be described below). Since coders 16 will almost always see "left clavicle" or "right clavicle" in the medical record, it is efficient to also pre-define hyperslice representations of each.

Many terminology options are commonly described by a phrase rather than a single word. Any mechanism keeping track of the relationship between terminology options and hyperslices needs to be able to distinguish a phrase ("left clavicle") when it occurs from its constituent parts ("left" and "clavicle") even when both are associated with hyperslices.

The Hyperslice Dictionary

In exemplary embodiments, the system 10 creates a hyperslice dictionary prior to conducting hyperslice-mediated autocoding or computer assisted encoding. This dictionary is a collection of relationships between known terminology options and hyperslices, where the terminology options are expressed in the terms that the computer or coder 16 are likely to encounter in the medical record. These expressions may be: (1) English words or phrases when ICD-10-PCS is used in U.S. hospitals, (2) words or phrases in other human languages if ICD-10-PCS were to be adopted for use outside of the U. S, or (3) concept identifiers in Electronic Health Records (EHRs). Concept identifiers could include, for example, SNOMED-CT concept identifiers and/or Health Data Dictionary (HDD) numeric concept identifiers.

In some embodiments, the system 10 uses English terms to express the terminology options, although other language terms are also possible. Accordingly, the hyperslice dictionary can be expanded to include the other expressions. In a preferred embodiment, the system 10 interrogates a dictionary containing relationships between known input terms and hyperslices representing known terminology options to determine a set of valid terminology options based on input by the coder 16. The creation of a hyperslice dictionary could include: 1) computer analysis of the PCS Code Definition Database (PCDD), 2) review by medical coding experts (nosologists), and 3) mining of other terminology sources.

Hyperslice Dictionary Creation by Computer

The PCS Label Table in the PCDD contains a row for every PCS character that is used for each axis of classification for each section. When duplicates are removed (e.g. "Z" in axis 7 means "no qualifier" in nearly every section), there are about 3,000 discrete entries (as of 2011). These can be thought of as fundamental "building blocks" of PCS. Each represents a terminology option associated its own special character, and generally is not represented in PCS some other way. The terms associated with the characters in the PCS Label Table are the internally-defined PCS terms, which may or may not be exactly consistent with conventional use outside of PCS.

The hyperslice dictionary may be embodied in a table, or in a database, such as a relational database system, or an object database system. Other implementation are also possible, as will be evident to skilled artisan.

The PCS Label Table provides a preferred starting point for creating the hyperslice dictionary. Each entry identifies a Section, an axis of classification, a character value in that axis, a specification, if any, of other axes on which the character value's meaning depends, and the English word or phrase used to label that character value for that axis in that section in the PCS tables. A hyperslice dictionary entry is constructed by placing carats in all axes not mentioned in the label definition to define the hyperslice, and using the English word or phrase to define the terminology option. For example, for axis 4, section 0, character value D denotes "Right Hand Artery" when axis 2 (body system) is a 3 (Upper Arteries). With this information, the program creates the following hyperslice dictionary entry:

| Terminology option | Hyperslice |
|---|---|
| Right hand artery | 03^D^^^^ |

While the program is creating hyperslice dictionary entries from the PCS Label Table, it can also apply a set of heuristics to create broader hyperslices for the individual words or phrases that make up the terminology option when they can be decomposed. In the example above, this entry is one of the places where "right" is distinguished from "left," and so gets added to the definition of "right" (some body parts, like lobes of the lung and heart chambers, are not functional mirror images of each other and so should not be separated from their "left" and "right" designations). "Hand artery" is partially defined here, as is "artery." Whether this represents a partial definition of "hand" is not clear—the other uses of "hand" in PCS may all refer to the gross anatomy, rather than embedded sub-systems.

These heuristics generally constitute a compromise between errors of type 1 (failing to capture a terminology option that might be useful to coders 16 when dealing with the actual text of the medical record) and errors of type 2 (associating PCS codes with each other in a "terminology option" which is not medically meaningful, but instead a jumble of codes which happen to use the same word in their labeling). Optionally, identification and resolution of both kinds of errors can be resolved in a second phase of hyperslice dictionary creation, where nosologists review the hyperslice definitions, adding slices where type 1 errors occurred and removing those where type 2 errors occurred.

In some embodiments, a compromise between type 1 and type 2 errors is achieved by applying three primary heuristics:

- Identify a set of directional words (left, right, upper, lower, superior, inferior, etc.) and for every term using one of those, create the slice both with and without the directional word.
- Ignore prepositions, articles and a few other common English words.
- Avoid the heuristics altogether for highly specialized sections, because it would create a disproportionately large number of new slices representing comparatively few codes (e.g. section F Rehabilitation and Diagnostic Audiology).

After the PCS Label Table has been analyzed, the dictionary creation program can then process two other sources in the PCDD, the PCS Index Table and the PCS Reference Table:

- The PCS Index Table contains links between common terms (for example those found in ICD-9-CM and CPT) with the PCS tabular section of the PCS document, where the equivalent PCS code can be found. Sometimes the index entries specify down to the code level (for example, Esophagogastroscopy=0DJ68ZZ). A code itself can be a valid hyperslice. More often the term only identifies a table, or a table plus a body part (e.g. epistiotomy=0W8N). The program creates the hyperslice/term combination by adding carets to all unspecified axes of classification. These entries can benefit substantially from nosology scrutiny in the next phase.
- The PCS Reference Table contains definitions and examples of most PCS character labels, and the Body Part Key. Even when the definitions are too long to be used for defining hyperslice/terminology option relationships, the procedure examples given in definitions can still be useful. The Body Part Key entries are structured the same as the PCS index, and hence are processed via the same technique as outlined above.

Computer generation of the hyperslice dictionary using the above methods can produce about 6,000 entries.

Consolidation and Counting

After the PCDD has been processed for hyperslice/terminology option relationships, the results can be consolidated and counted. The same term can be encountered more than once (e.g. a term is both in the index and an example in the reference section). Terms may be built up from partial definitions (e.g. "eyelid" may be represented as "lower eyelid" and then later as "upper eyelid").

As the dictionary is synthesized according to the processes defined above, the system 10 preferably maintains a list of hyperslices for each recognized term. The system 10 can use, for example, an AVL tree to maintain the set of terms, and for each term the set of hyperslices associated with it. Use of AVL trees avoids posting duplicates. Once all term-hyperslice pairs have been listed, the hyperslices for each term must be consolidated. Consolidation is generally a recursive process which operates, for each term, as follows:

- Sort the hyperslices in lexicographically ascending specification order. (Since they are maintained as an AVL tree, this only means unraveling the AVL tree into a sorted list.)
- For each hyperslice, consider all the hyperslices which are lexicographically higher than it.
- If any pair of hyperslices so considered has six of the seven axes of classification identical, replace the two hyperslices with a new hyperslice, copying the six identical axes and applying an "or" Boolean operation on the bits of the seventh.
- If any combinations were discovered for a term, then recursively reapply the consolidation algorithm, since the new, combined, hyperslices may combine with others that the original hyperslices were unable to combine with.

When the consolidation is complete, the hyperslices are preferably counted against the PCDD, using the counting routine outlined above. Counting reduces the size of the resulting hyperslices and makes nosology review more efficient by keeping points in the PCS-n-section spaces that contain zero codes from being shown to nosologists.

Nosology Review of the Hyperslice Dictionary

Nosologists can then review the results of the computer generation of the hyperslice dictionary. This review can assist in identifying and correcting the following example errors and omissions:

- The hyperslice associated with a terminology option is too broad and must be narrowed to conform to current medical terminology.
- The hyperslice must be divided into two or more hyperslices (with concomitant extension of the terms) to make clinical distinctions not apparent to the computer.
- The hyperslice associated with a terminology option is too narrow and must be expanded to allow for approaches, body parts, devices or qualifiers that the source did not identify.
- The term is no longer used, or is ambiguous in meaning.
- The terminology option is too broad to be useful in abstracting procedure documentation into codes (the terminology option "procedure," if not filtered out upstream by heuristics, would be an example).
- A common terminology option is missing and must be added.
- A common abbreviation or alternate term for a terminology option in the dictionary must be added.

Figure 3:
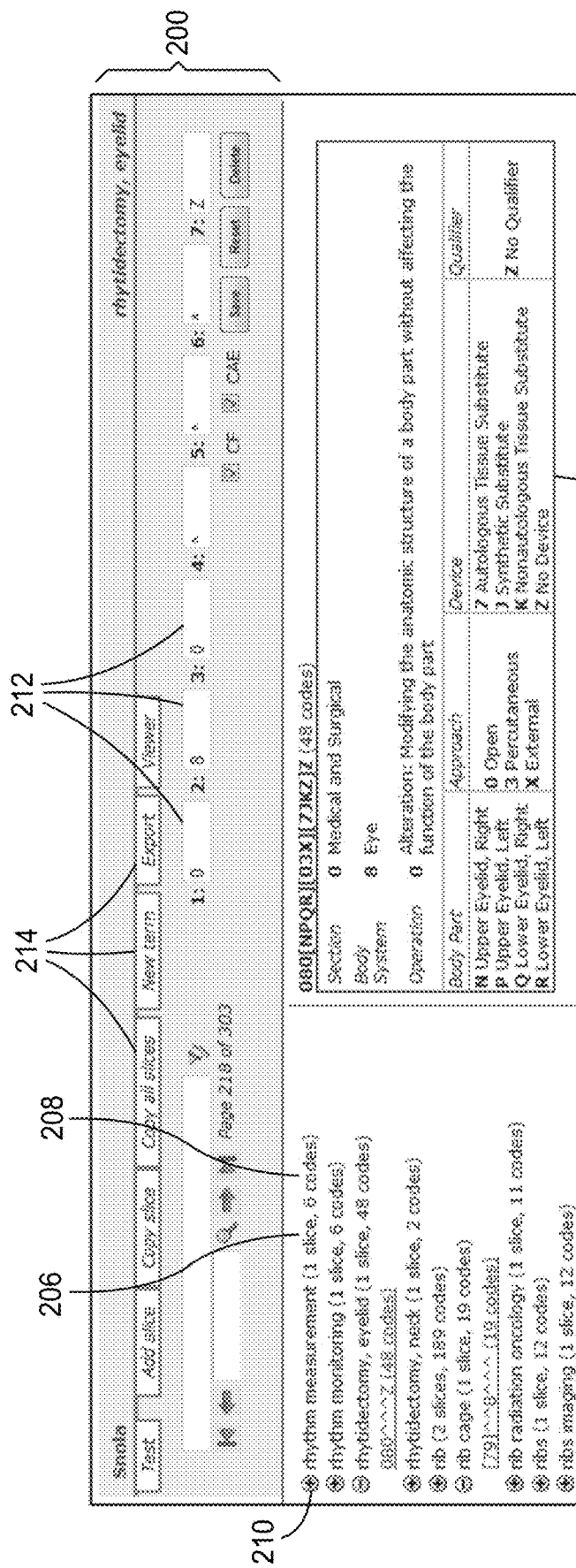
FIG. 3 is a partial screenshot showing a user interface of the system.

FIG. 3 shows an exemplary hyperslice dictionary maintenance tool (within the hyperslice dictionary manager 28) usable by a nosologist 20 to efficiently review 6,000 or more hyperslice dictionary entries. This screen shot, as viewed on a computer display, illustrates some of the advantageous features of this tool. These features can be accessed using a suitable cursor control device. A suitable cursor control device can be a mouse, trackball, pen, or touch screen. Such a device enables a user to "click" to select on a particular dialog box, icon, menu bar item, button, text field, or other feature in the graphical user interface.

As shown, the application screen is divided into three panes:

A control pane 200 across the top provides a user interface in which the user makes requests of the tool, as described below.

A terms pane 202, below the control pane and to the left, contains the list of terms in the hyperslice dictionary.

A hyperslice pane 204, below the control pane and to the right, displays details about the hyperslice currently being reviewed or modified.

The nosologist 20 uses the navigation control to select a page of terms to work on. By entering a hyperslice expression in the upper text area and pushing the filter button (denoted by the funnel), the nosologist 20 may restrict the review to only those hyperslices that satisfy desired conditions (e.g. only obstetrical procedures). Entering a term into the lower text area and pushing the search button (the magnifying glass), the nosologist 20 can bring a specified term onto the screen. The arrows allow paging through the terms, forward and backward. As shown, terms available for review are listed in the terms pane 202.

Within the terms pane 202, the total number of slices 206 and total number of codes 208 identified by those slices are listed. By clicking on the plus button 210 for a term, the user can see the slices associated with a term, and by clicking on a slice, the user causes it to be loaded into the right pane, the hyperslice pane 204. The hyperslice is conveniently displayed in standard PCS table notation so that the nosologist can see the complete official definition of the included codes.

When a hyperslice is selected, the control pane 200 contains the hyperslice edit control 212. Here, the nosologist 20 may alter the definition of the hyperslice by changing the contents of one or more of the axes boxes and clicking Save. The nosologist 20 may also "Delete" the hyperslice, "Reset" it to its original status if modified, or indicate under which circumstances the hyperslice-term relationship can be used ("CF" in this example designates the encoder 24 and "CAE" designates the autocoder 22). At any time, the nosologist 20 can click on menu bar options 214 at the top of the control pane 200.

The menu bar options 214 allow the nosologist 20 to request specific tool actions, as described in more detail below:

"Test" brings up an encoding system where the nosologist 20 can immediately see the impact of the hyperslice changes just made.

"Add slice" allows the nosologist 20 to add another slice to this term.

"Copy slice" allows the nosologist 20 to specify a new term to be added to the dictionary, with the current slice as its initial definition.

"Copy all slices" allows the nosologist 20 to specify a new term to be added to the dictionary, with all the slices of the current term as its initial definition. It essentially creates a synonym, which can then be altered if necessary.

"New term" allows the nosologist 20 to specify a new term to be added to the dictionary, and then takes her to a PCS exploration tool (the CTT Viewer) where the nosologist 20 can define the slice that will be the initial definition of the term.

"Export" saves the current hyperslice dictionary in an ASCII file on her computer.

"Viewer" invokes an ICD-9/ICD-10/General Equivalence Mapping (GEM) exploration tool, where the nosologist 20 can find all the information that is in the HHS official documents for ICD-10-PCS (as well as ICD-9-CM and ICD-10-CM and the relationships between them).

Expanding the Hyperslice Dictionary

Optionally, other sources of medical procedure terminology can be used to expand the hyperslice dictionary. Two primary examples are Current Procedural Terminology (CPT, copyright American Medical Association) and SNOMED-CT (copyright National Library of Medicine). While both sources contain a wealth of terms, there is no simple linkage between those terms and PCS hyperslices. To use such sources, the process does the following:

1) Searches the existing hyperslice dictionary and discards terms already defined.

2) Provides a list of new terms that nosologists 20 can use to add terms to the hyperslice dictionary, developing hyperslice definitions via clinical judgment in the process.

Optionally, the process of recasting the hyperslice dictionary into another language, or linking it to another procedural coding system is only partially automated. If machine-readable translations between languages, or between English terms and codes, exist, they may be used to create an initial hyperslice dictionary based on their presumed equivalence with English terms. If so, it is preferable for clinical review of the results to be conducted afterwards, since medical expressions in other languages and systems are not guaranteed to be equivalent to their English transliteration.

Exemplary Coding Workflow

The use of hyperslices by the system 10 is demonstrated by way of the following example. In this description, steps carried out by the user (e.g. coder 16) are described along with corresponding processes executed by the system 10.

Figure 4:
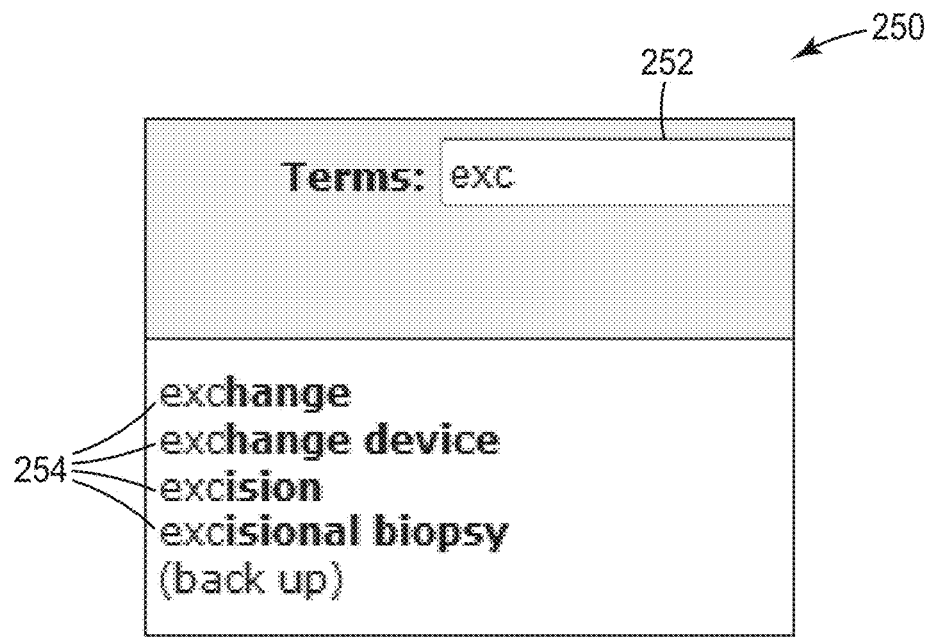

FIG. 4 shows the first step in a screen 250 of the hyperslice dictionary maintenance tool. The coder 16 begins by typing in terms in the medical record believed to be relevant to the procedure code of interest. In some embodiments, terms are found by clicking on highlighted words in an electronic copy of a document. The system 10 then pre-highlights in bold face all matching terms found in the hyperslice dictionary. The terms can also be read directly by the computer during an auto-coding analysis. In this example, the coder 16 has typed the first three letters of "excision" into a dialog box 252 in the test screen 250 and a list of all the "exc . . . " terms 254 comes up.

Figure 5:
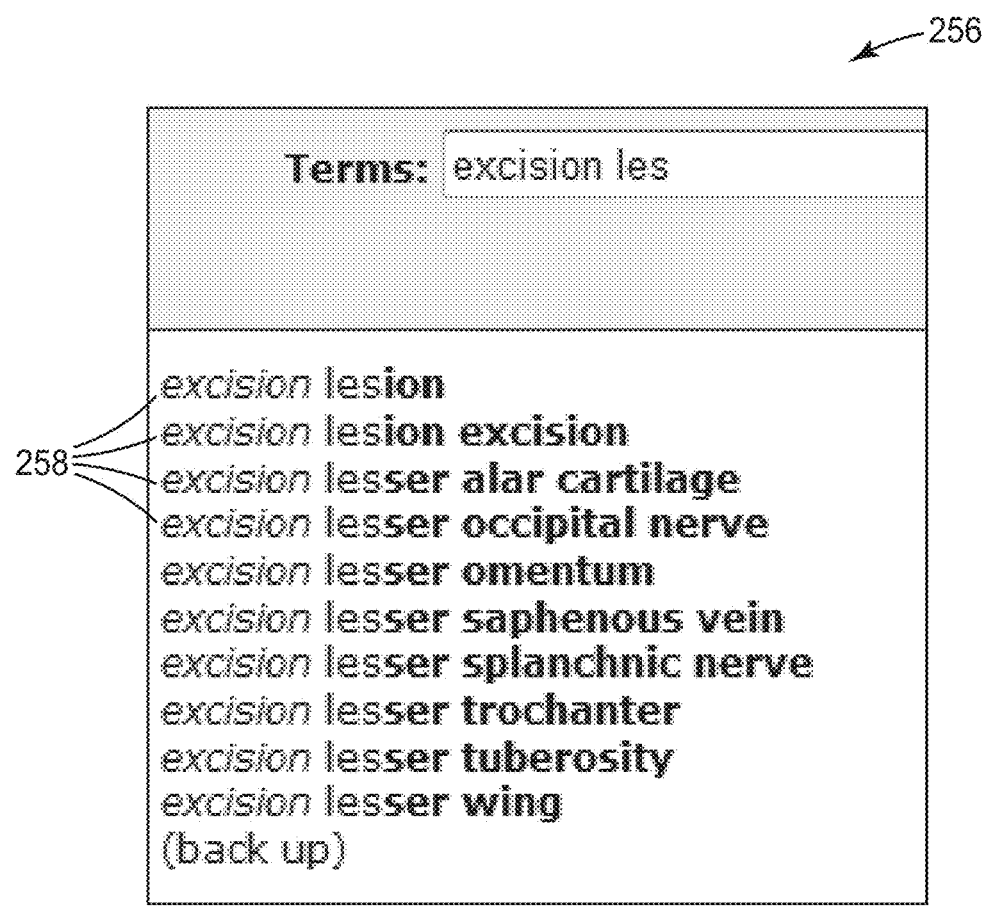

FIG. 5 shows updated screen 256 after further information has been entered. In this example, the coder 16 had chosen "excision" and now continues typing, intending to type "lesion." After the coder 16 has typed "les . . . ," the screen shows the matching terms 258 shown in FIG. 5. From here, the coder 16 then chooses "lesion" and starts typing "brain," as shown in screen 260 in FIG. 6. At this point, the coder 16 decides that this is all the information that will be entered directly, chooses "brain," and finally hits the "Enter" key. This brings up graphical user interface 300 shown in FIG. 7.

Figure 7:
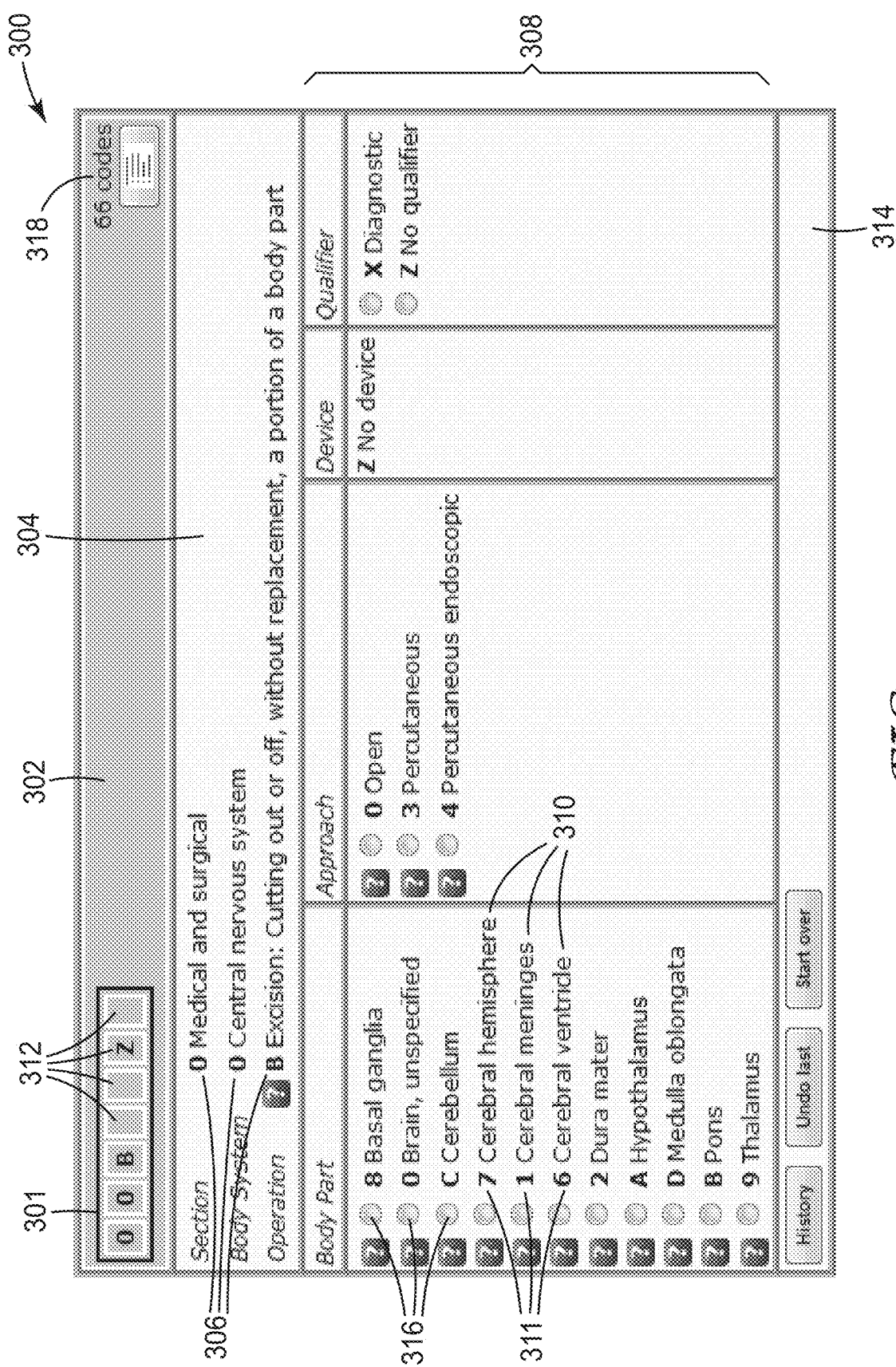

FIG. 7 demonstrates how the interface 300 can assist the coder 16 by facilitating the complete specification of a partially populated procedure code 301. As shown, the system 10 uses one or more of the provided input terms to determine a set of valid terminology options. In this particular case, hyperslice analysis of "excision," "lesion" and "brain" yields the following results:

The desired PCS code is in the medical/surgical section (axis 1=0)

The body system is "Central nervous system" (axis 2=0)

The root operation is "Excision" (axis 3=B).

The excised body part is some part of the brain (11 terminology options for axis 4).

The coding system allows three possible approaches (3 terminology options for axis 5).

For brain excisions, no device is ever coded (axis 6=Z).

An excision can either be a biopsy (X=diagnostic) or therapeutic (Z=no qualifier) (2 terminology options for axis 7).

The axes of classification above can be analyzed by interrogating the hyperslice dictionary to identify procedure code characters associated with input terms and the corresponding character value (or values) associated with each of the characters. This information is then displayed in a modified PCS table format, with a partially unpopulated seven-character ICD-10-PCS code 301 concurrently displayed on the left side of a first pane 302. On the upper right side of the first pane 302 is a code count 318 indicating that 66 valid procedure codes can be derived from the partially populated procedure code 301. Below the first pane 302 is a second pane 304 listing the known character values 306 (here "0," "0," and "B") for the first three characters of the code 301, respectively.

Again referring to FIG. 7, the lower two-thirds of the interface 300 includes a third pane 308 providing four columns representing the last four characters of the code 301, respectively. Of these four columns, the first, second, and fourth columns each present two or more terminology options 310 (along with respective character values 311) for each unpopulated character 312 in the code 301. Finally, a bottom-most pane 314 provides the coder 16 with additional options to examine the search history, undo previous entries and start over.

Figure 8:
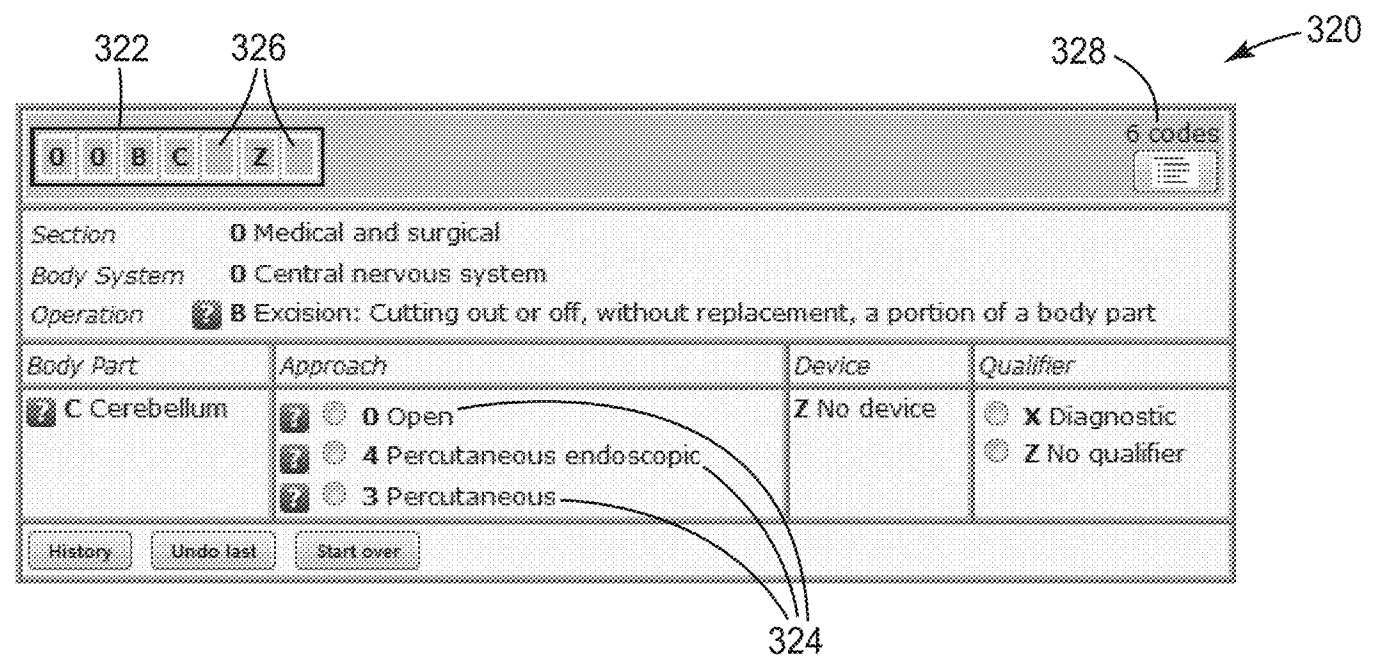

The coder 16 clicks on radio buttons 316 to provide selection input associated with any of the corresponding valid terminology options 310 to progressively populate the procedure code. Here, the coder 16 can narrow the available choices down to a single ICD-10-PCS code with three successive selection inputs. For example, choosing "C" (representing "Cerebellum") for Body Part in the first column of the pane 308 brings the coder 16 to the updated interface 320 shown in FIG. 8. As shown, the updated interface 320 presents an updated procedure code 322 now including the new character value "C." From this screen, clicking on "0" (which represents "Open") in Approach and Z (which represents "No qualifier") for Qualifier yields a confirmation screen 400 for the now fully-populated code 402.

The system 10 updates the user interface to display to the coder 16 all valid terminology options, based on the information already provided, at each step of the coding process. Referring back to FIGS. 7 and 8, for example, the system 10 responds to each selection input from the coder 16 by updating the user interface 300,320 to present revised valid terminology options 310,324 associated with one or more of the unpopulated characters 312,326 of the code 301,322 for which there has been no selection input. By using hyperslices to incorporate the known information at each step, this feature can significantly improve the clarity and efficiency of the coding process. As shown in the upper right corners of FIG. 8, updating the user interface 320 includes re-counting and re-displaying a code count 328 showing the total number of codes corresponding to the revised terminology options.

FIG. 9 shows a confirmation screen 400 in official PCS table format. As shown, each character of the procedure code 402 is now populated and the fully specified code 402 is presented to the medical coder 16 for verification. From here, the coder 16 can access a toolbar 404 at the upper right of the table 400 to "Accept" the code, "Revise" the code by going back to the PCS table representation with choices, "Copy" the code and record another with slightly different options, or "Remove" it and start over.

Alternatively, the coder 16 could arrive at the same outcome by entering all of the choices as terms. For example, in the test screen 250 (shown in FIG. 4) the coder 16 could have entered: "open therapeutic excision cerebellum." In this case, the system 10 would bring the coder 16 directly to the confirmation screen shown above. Similarly, an auto-coding engine, once it has isolated those terms from the medical record as being relevant to a procedure performed on the patient, would require no human intervention to then produce the appropriate PCS code.

Representing Terminology Option/Hyperslice Relationships

A major factor in supporting the coder-encoder interaction illustrated above, with the rapid response users have come to expect from online products, is an efficient representation of the terminology option/hyperslice relationships. This is provided by the Hyperslice Dictionary Repository (HDR), a database consisting of three tables:

The Term Table contains two columns:
   A term-ID—internally generated integer uniquely representing the term.
   The term as a character string. A term may be a word or a phrase. Terms will often be initial segments of other terms.

The Slice Table contains four columns for each hyperslice known to the repository:
   The term-ID to which this slice belongs.
   The array of seven 34-bit strings representing the characters allowed by the slice for each of PCS's seven axes of classification.
   The 7-bit string representing which axes were left unspecified in the slice's original definition.
   The code count for this slice.

The Search table implements a Patricia Tree representation (see below) of the known input terms in the dictionary. The Search table contains five columns:
   A node-ID—an internally generated integer uniquely representing each node in the Patricia Tree of terms.
   A letter, denoting the next letter to be matched against user input.
   A string, the subsequent string, which may be empty, which must be matched in the input before the program can move to the next node.
   The next-node-ID, identifying the next node to query if the letter and subsequent string match the input. If zero, it indicates that there are no more options to consider.
   A term-ID if, having matched the input to this point, a term has been recognized.

In a setting where the HDR can be represented in a sufficiently powerful relational database management system (RDBMS), and where usage is light, only the first two tables can be used and the RDBMS can be relied upon to fetch relevant slices to support the algorithms outlined below. Optionally, the two tables could be joined to one, where the slice index is the term itself instead of the term-ID. However, empirical tests have shown that the Patricia Tree implementation, explained below, provides superior performance and can be implemented easily on the desktop without the intervention of a large, expensive, RDBMS.

Patricia Tree Term Representation

To construct the HDR, the terms are first arranged in a modified Patricia tree. In this representation, each letter of a term is represented in a node, which carries references to:
- all nodes representing the next letter when this letter matches
- all nodes representing alternate letters when this letter fails to match.

To save space and processing time, the HDR-modified Patricia tree nodes can also carry a string which represents the characters, following the node's initial character, that have no alternatives in the repository. These are the nodes which need to be matched to an input before the next single-character choice needs to be made.

FIG. 10 shows an excerpt 450 from the HDR's Patricia tree representation of those nodes beginning with the letter "b." The easiest way to illustrate this is to assume that the system 10 has an input term and seeks to match the term with the contents of the tree.

Each line of the example represents one entry in the Patricia tree. The level of indentation indicates where the characters on the line must match the input. The "b" on line 01 must match the first character, the "a" on line 02 must match the second, the "ck" on line 03 must match the third and fourth, etc. When the characters match, if more characters are available in the input, the system may move on to subsequent lines, if any, which are further indented. A number in brackets on the line indicates the term-ID of a term if a term known to the HDR is recognized by arriving at the node and satisfying its requirements. A tilda (~) is used to represent a blank when it occurs all by itself in a node.

All the terms represented by this sample must start with "b." No other node shown here is at the same level of indentation ("c" starts about 330 lines further down). The next node after "b" is "a," so all lines underneath it, until the algorithm encounters one at the same level, must start with "ba." This sample shown here is too small to show that "be" starts about 45 lines after "ba," so the algorithm is inspecting most of the terms in the HDR that start with "ba."

If the third letter is "c," then the fourth letter has to be "k," or there is nothing in the HDR matching the input. The algorithm now recognizes "back" and it is a defined term, ID number 405. However, if "back" is followed by a blank (the tilda on line 04 of the example) then that term may be followed by "fascia," yielding "back fascia" (ID 406), or by an "s." If an "s" is present, then the algorithm can recognize "back skin" (ID 407) or "back skin radiation oncology" (ID 408) or "back subcutaneous tissue" (ID 409). Those are the only terms known to the HDR which start with "back."

Another way to illustrate this representation is to consider what a matching algorithm does to recognize an input phrase, say "bandage removal." Starting with the first letter of input, "b," the algorithm will have gone directly to the first line of our example (01). There is no hyperslice associated with "b" by itself. Moving to the second letter, "a," it matches line 02. Once again, no hyperslice applies. There are six alternatives showing for the third letter: "c" line 03, "f" line 10, "l" line 11, "n" line 16, "r" line 29 and "s" line 32. The input here is "n" so the algorithm moves to line 16, where it discovers the "n" must be followed by "d." This is the case, so the algorithm moves on to the fifth letter, which must be either "a" line 17 or "l" line 23. No other options are available. The "a" matches our input, as well as the "ge" in positions six and seven.

At this point the algorithm recognizes "bandage" and observes there is a term (ID 414) associated with it. There is further input, but if that input cannot be recognized, the algorithm could still use "bandage" to start down a coding path. However, the blank at position eight is matched by line 18, yielding three options for position 9: "c," "d" or "r." The "r" matches, taking the algorithm to line 21. Then, "emoval" matches the rest of the line. All of the input is used up and term 5841, "bandage removal," has been recognized. In the end, only six comparisons were required to determine the hyperslices for a fifteen-letter term.

This illustration has been simplified to illustrate the method. Preferably, the implementation also performs one or more of the following:
- folds the input line to all lower case
- removes redundant white space, reducing word separation always to a single blank
- looks up matched terms in the terms table so that they may be reported with the proper case. (For example, "bartholin's gland" on line 31, is reported as "Bartholin's gland" once term 423 is retrieved from the term table).

Support for common misspelling is provided by transforming the Patricia tree using a sound-alike algorithm before storing it in the HDR (preserving the characters needed for disambiguation), and then applying the same sound-alike algorithm to the input of the coder 16.

Backing Up Rules

Suppose, in the example above, the input had been "bandage left arm." The coder 16 does not know what operations on bandages PCS encodes, and wants to be asked, but does know that the bandage in question was on the left arm. According to the algorithm described above, the system 10 would have found "bandage" (term 414~see line 17), discovered that it could be followed by a blank (line 18) but from there the only options are "c," "d" and "r," not "l."

Sometimes one of the following situations occurs:
- a term has been recognized (for example "bandage"), or
- the term is followed by white space (here, a blank) If so, the hyperslice term recognizer accepts the recognized term, and then backs up to the beginning of the Patricia tree and attempts to recognize the remainder of the line (here, "left arm") independently.

The backing up rules are applied recursively to the entire input. In this example "left arm" will not be recognized as a term in itself, so the result will be three independent terms: "bandage" and "left" and "arm." When a word is not found in the HDR, it is ignored so that the backing up rules may be applied to the remainder of the input. For example, "bandage on left arm" would ignore "on" so "left arm" could still be considered. In some embodiments, input terms not found in the hyperslice dictionary are also ignored.

The net result of the recognition algorithm is a breakdown of the input line into a list of terms, where each term is tagged with a term-ID. The term-ID zero means "not found." For example, the input "bandage on left arm cha" (a partial input on the way to "bandage on left arm changed") would result in terms shown as follows:
- bandage—term 414
- on—term 0
- left—term 2482
- arm—term 291
- cha—term 0

Combining Terms

Once the input terms have been found in the input, their associated hyperslices are intersected to narrow down the set of possible codes that the terms represent. The presumption behind this operation is that the terms are implicitly joined by a Boolean "and" operation. For example, "bandage on left arm" means "bandage and left and arm." It is left to the coder 16 or auto-coding software to assure that the terms supplied to the system have such an inclusive relationship.

Figure 11:
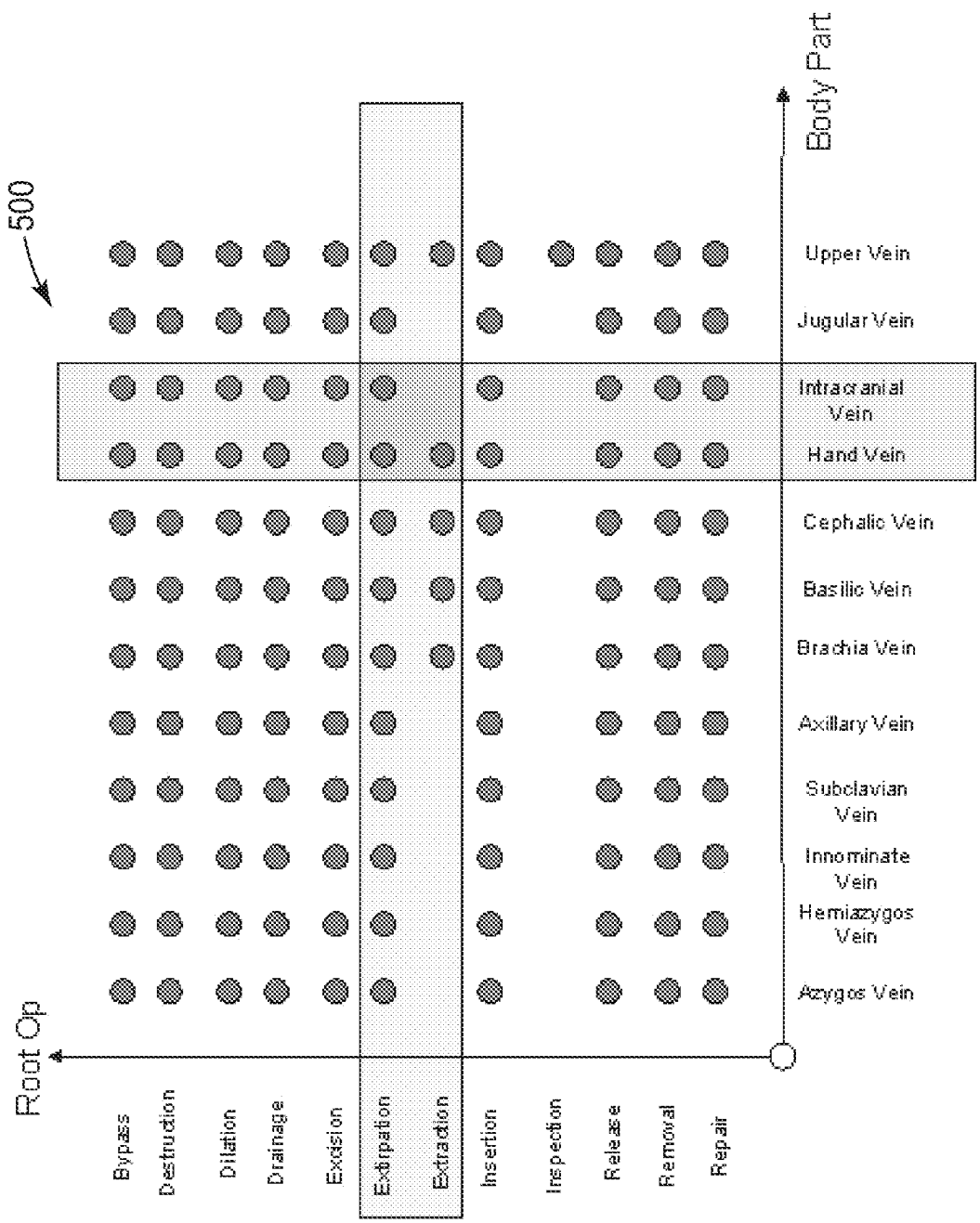
FIG. 11 is a diagram showing the intersection of two regions within the multi-dimensional abstract space referred to in FIG. 2.

An intersection of the hyperslices associated with entered terms will identify those codes in PCS that satisfy the meaning of the terms as embodied by the hyperslices. This is illustrated in chart 500 in FIG. 11, which shows only two dimensions of the six-dimensional PCS-0-section space.

Where the intersection results in one code, the system 10 can proceed directly to the code confirmation screen. When it results in more than one code, the system 10 can present a modified PCS table, allowing the coder 16 to make what choices are necessary to capture the code needed. When it results in a code-empty region, the intersection algorithm can optionally ignore the terms causing the emptiness, thereby providing some valid codes for the coder 16 to work with.

Figure 12:
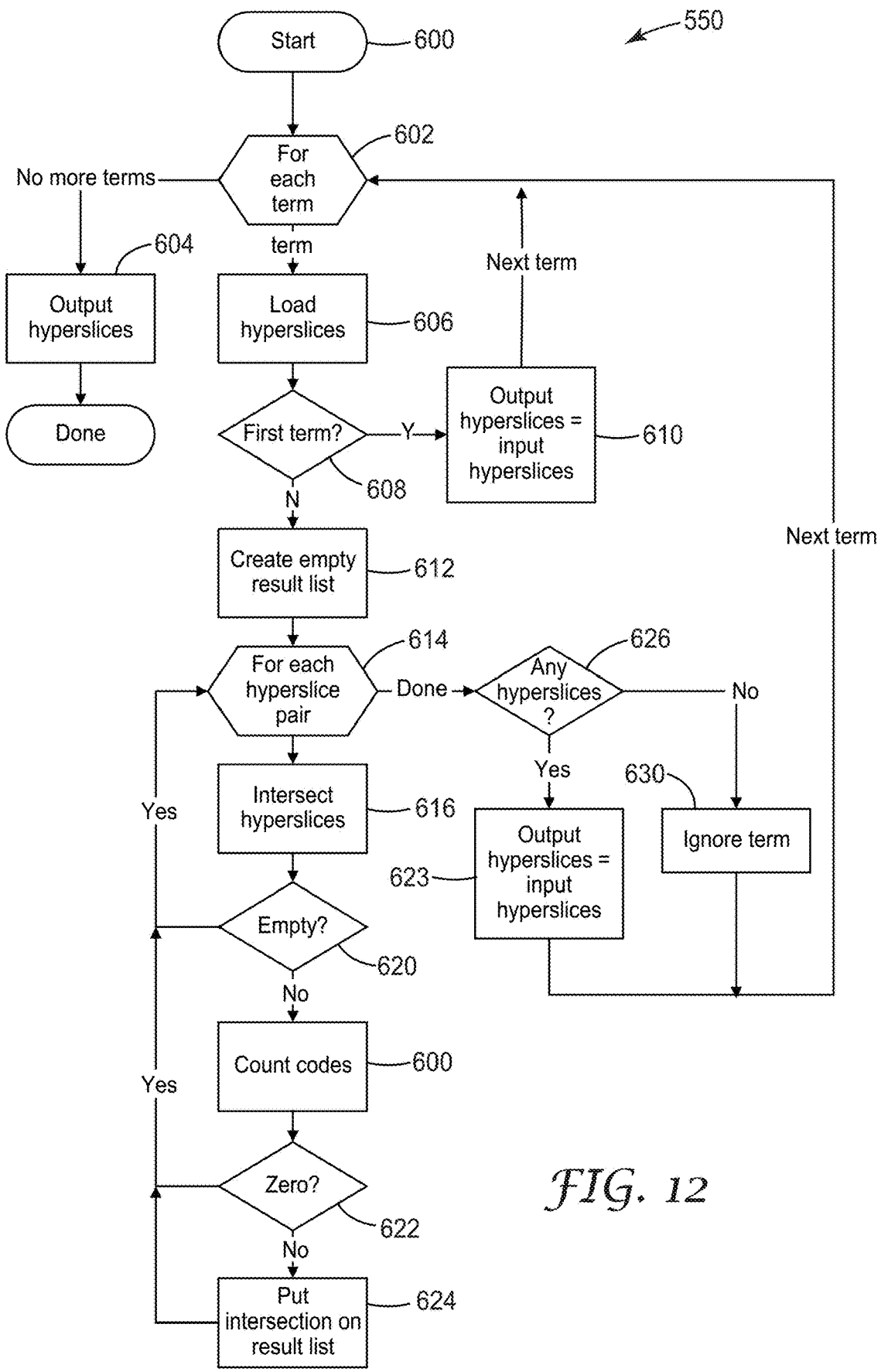
FIG. 12 is a flowchart showing a process for combining terms in the system.

To achieve this, the term-combination algorithm operates according to flowchart 550, shown in FIG. 12. Beginning at block 600, the term-combination process aims to create an "output list" of hyperslices (block 604) which represents all of the PCS codes that satisfy the meaning of the terms supplied by the coder 16. This list is initially empty. The process is repeated for each term (block 602) with a non-zero term-ID found in the input. The term will have one or more hyperslices associated with it in the HDR. Those hyperslices are loaded (block 606). Note that these hyperslices are already represented as bit strings in the HDR, so conversion from hyperslice specification to hyperslice representation is not necessary, having been done at the time of the creation of the HDR.

If this is the first (or only) term in the input (block 608), then its hyperslice list is moved to the output list (block 610), and the process moves on to the next term, if any. For all the other terms in the input, the process creates an empty "result list" (block 612). The process the proceeds to populate this "result list" with hyperslices that are intersections of the results obtained by earlier terms (the "output list") and the hyperslices associated with this term (the "input list").

It considers each hyperslice pair (block 614), consisting of a hyperslice from the output list and a hyperslice from the input list. The pair is intersected (block 616) using the hyperslice intersection method described above. If the result is empty (count=0) (block 618) then the process moves on to the next pair. The input hyperslice is not discarded yet—it might intersect with some other hyperslice on the output list. The intersection, requiring only a few bit-manipulations, is fast enough to compensate for the N-squared nature of the pairwise intersections (it is beneficial that only a few terms, like "left" and "right," have more than a few hyperslices—the great majority only have one—and the large ones are rarely used together).

If the intersection is not logically empty (i.e. represents no points in the PCS-n-section space) then the code count method, as described above, is used (block 620) to compute how many actual PCS codes are identified by the intersection. This is a relatively time-consuming part of the process, so it is not executed unless all other, faster, decisions have already been made. Further, the time-demand of the code counting can be limited by the following heuristic: if the count reaches some threshold (100, for example), then stop counting. The coder 16 may know there are codes in the hyperslice, and the routine that presents them to the coder 16 can then find all of them.

If codes are found in the hyperslice (block 622), then it is put on the "result list" (block 624) and the process continues with the next pair. Otherwise, it continues with the next pair without discarding the input hyperslice, as it may yet find some codes when intersected with other hyperslices on the output list.

After all the output-input hyperslice pairs have been intersected, the result list may or may not have hyperslices on it. If it does (block 626), then that means that at least one of the hyperslices associated with the term overlaps at least one of the hyperslices associated with earlier terms. In this case, the process replaces the "output list" with this "result list" (block 628) and moves on to the next term, if any.

If the "result list" is empty, then nothing has overlapped. This means that the information the term is bringing to the table does not intersect with what the user has specified in earlier terms. There are three ways the process could deal with this situation:

Stop and inform the coder 16 that the terms entered are mutually exclusive and allow the coder 16 to try again.

Ignore the term (block 630), maintaining the output list obtained before it, and see if any other input terms can be used to reduce the result space. This gives considerable priority to the order in which the terms are entered.

Having established, via nosology expertise, hyperslice priorities, or weighting rules for establishing hyperslice priorities, choose the hyperslices with the greatest priority or weight. For example, more specific (i.e. smaller) hyperslices could take precedence over more general hyperslices.

Try all combinations of input terms to find the ones that meet some criteria of optimality (perhaps yielding the smallest non-empty result space), ignoring the rest.

In this preferred embodiment, the second option (block 630) is used. Taking the terms in the order in which they were entered gives control to the coders 16, who can learn how best to interact with the system 10 over time. However, in an auto-coding setting, a different strategy may be preferred. Since there is no coder 16 interacting with the system 10, the fourth option, despite being computationally intensive, may be superior.

In the exemplary embodiment described above, the size of the working hyperslice decreases or stays the same as new input terms are added. This is because the process gives priority to terms in the order in which they are provided by the user. For example, if the user starts with "laparoscopic" then "resection" then "liver," then the term "liver" is ignored (as laparoscopic resection of the liver is not in the coding system).

Optionally, the system uses a weighted priority system. For example, such a system could give a higher weight to operation and body part than to approach. In this case, the term "laparoscopic" would get ignored. In that case, the number of codes for "resection liver" might be higher than the number of codes for "laparoscopic resection," so the addition of "liver" to the mix might increase the number of codes. This type of system may be preferred if nosologists 20 have defined these weights.

Displaying Results

The term-combination process results in one or more hyperslices, encompassing all the PCS codes allowed by the set of recognized terms, being joined together by a Boolean "and" operation. Each hyperslice is code-counted. If there is more than one hyperslice, or the one hyperslice contains more than one code, then the preparation of the modified PCS table, with options for the coder 16 to choose from, can also use the PCDD as follows:

For each axis, the bits still on in the result hyperslice are converted to character values for the axis.

The PCS Label Table is queried using the axis and character value as key. Where multiple entries for the same axis/value are found, the dependencies are checked against the other character values allowed by the hyperslice. Options not satisfied are ignored.

The table is then constructed. For axes where only one character value is found, the value is shown without a radio button, though "help" icons may be supplied so that the user can see the PCS definition of the label showing (the table shows the labels that PCS uses, which will often not be the same terms as the coder 16 entered to start the process).

Where more than one character is found, radio buttons or other user interface controls allowing a choice are presented, along with "help" icons, so the coder 16 can choose which axis to restrict and which code to restrict it to.

When the user makes a choice, the choice is registered as another input hyperslice, with a computer generated "term" drawn from the label table. For example, if the user selects "Open" in the fifth axis in the med/surg section (defined as Approach), it is treated as input hyperslice "0^^^0^^" with input term "Approach=Open." The term combination process is then re-executed.

The benefit of the last step above comes about because the PCS-n-section space is only sparsely populated with actual PCS codes. For example, suppose both Body Part and Approach remain to be chosen. When choosing the Body Part, the coder 16 may also be choosing (or limiting choices of) Approach, since for some Operations and Body Systems, not every Body Part admits of every Approach. Re-executing the term-combination process allows the system 10, with little cost, to present only those options that are actually available given all the choices made so far, or even go straight to the confirmation screen.

Other Methods of Interaction

In the examples presented, the choices of the coder 16 have been displayed as modified PCS tables, similar to those used to represent PCS codes in the official literature, except with additional icons for making choices and requesting help. In various embodiments, the hyperslice representation supports other forms of coder query and input.

In some embodiments, the system 10 queries the coder 16 with a series of questions, where each question is associated with a respective unpopulated character of the procedure code. Here, the system 10 asks one question at a time rather instead of presenting all options to the coder 16 at once. Alternatively, the two modes could also be available simultaneously, under coder control and/or chosen via preferences. In the one-question-at-a-time mode, the system 10 chooses which axis to ask about first when more than one axis remains to be filled in. This decision can be mediated by hyperslices.

Figure 13:
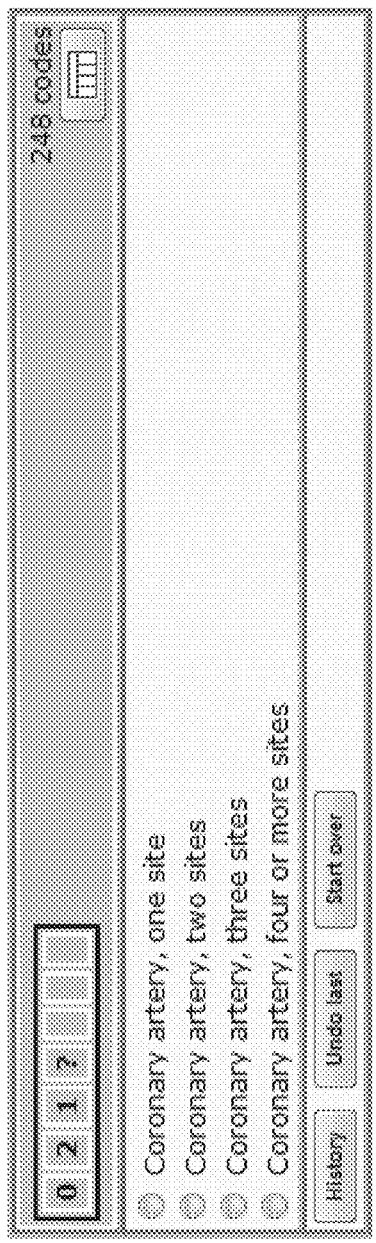
Figure 14:
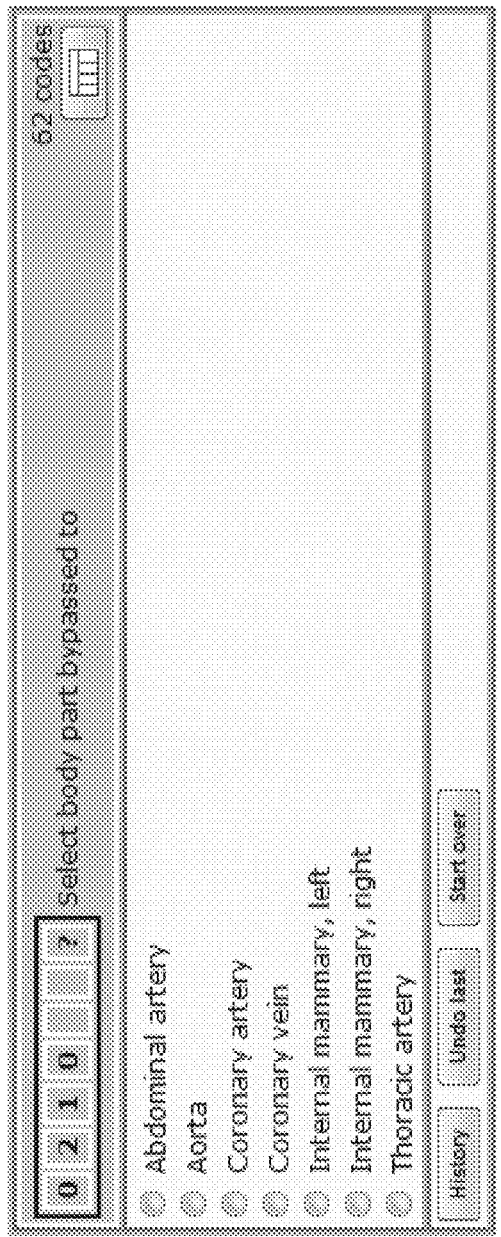

To enhance efficiency of the coding process, the preferred order could be at least partially based on the currently defined procedure code. Here, for example, the coder 16 has entered "bypass coronary artery" and is in one-question-at-a-time mode. FIG. 13 shows a query screen 700 presented by the system 10 to the coder 16. The number of sites bypassed (axis 4) is requested. After the coder 16 chooses one (for example, one site), the next question that comes up is shown in query screen 710 in FIG. 14. As shown, the system 10 has jumped to axis 7 and is asking for the body part bypassed to, while skipping over axis 5 (the Approach).

It knows to do this because it has been told that when the hyperslice resulting from term-decoding and user selection—regardless of the path the coder 16 used to get there—is contained within hyperslice "0^1^^^^," then a Bypass is being coded and the system should execute the following steps:
1) choose 4 Select the body part bypassed
2) choose 7 Select body part bypassed to
3) choose 5 Select approach
4) choose 6 Select graft or synthetic device used in bypass Hyperslices can be used to regulate any number of the functions the system 10 performs:

In what order to ask the coder 16 to fill in unfilled axes.

When to offer help, and what help to offer.

When to show anatomical diagrams and other decision aids.

When to give warnings.

When other codes might be needed or wanted by the coder 16 and what the coding paths for those codes would be.

When these are controlled by hyperslices, then the path the coder 16 takes—including backing up and revising previous choices—is irrelevant. The controlling hyperslice triggers action by the system 10.

Methods for Backing Up

Figure 15:
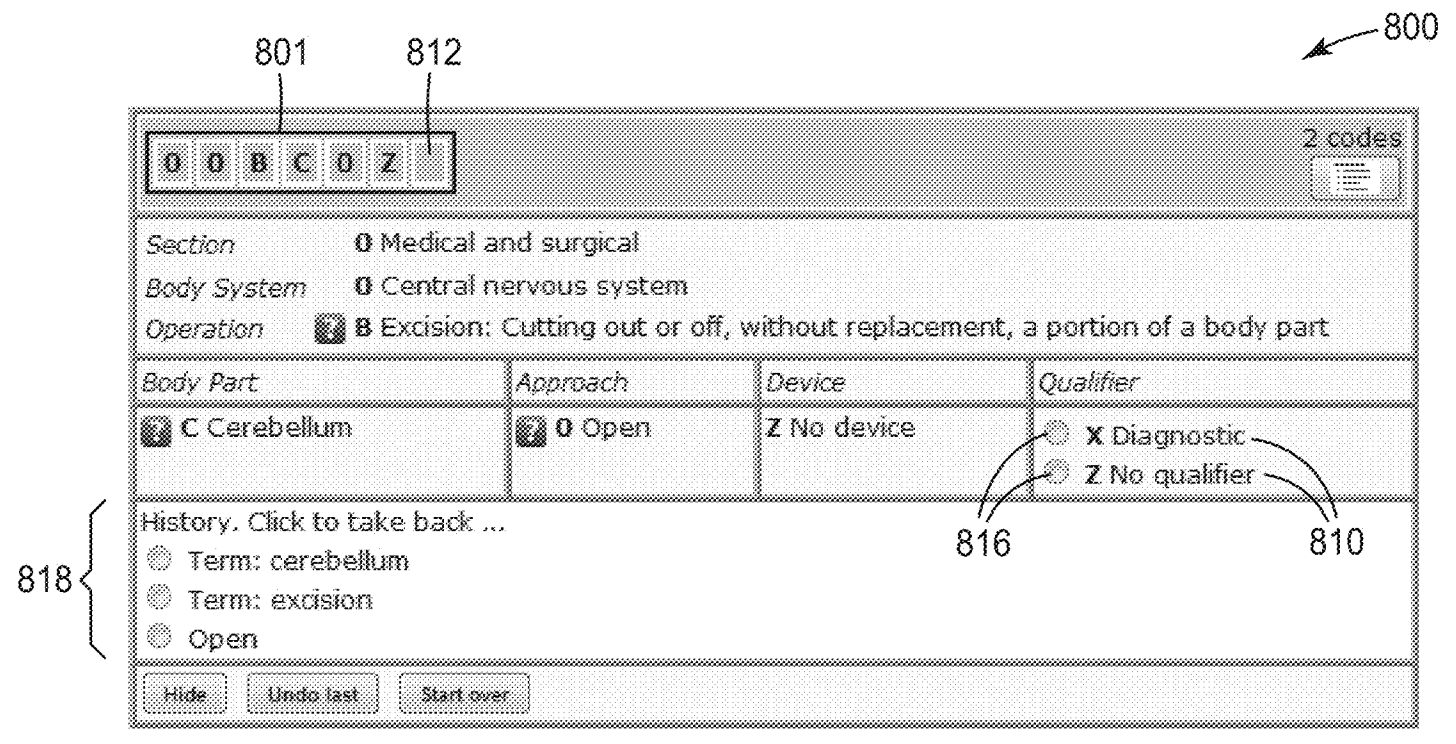

By keeping the list of recognized terms and user choices, the system 10 can present to the coder 16 a way to change his or her mind with respect to input previously provided. Advantageously in some embodiments, the coder 16 can discard the coding path being used and start over with new terms. To illustrate, consider the "cerebellum excision" example previously described in the user interface 300. Recall that the coder 16 has provided a series of selection inputs to progressively modify the valid terminology options 310 while the interface 300 is continually updated to present the modified terminology options after each selection input. Suppose, after choosing "open" for approach, the coder 16 wants to re-consider and clicks "History." The system 10 then displays interface 800, as shown in FIG. 15.

The interface 800 presents radio buttons 816 corresponding to terminology options 810 which the coder 16 can select to keep going (in this case, by choosing the Qualifier). However, the interface 800 also presents a pane 818 showing terms previously entered and choices subsequently made. The pane 818 invites the coder 16 to "take back" any one of these terms/choices. Thus, in some implementations, the coder 16 can provide additional input to correct a previously received selection input other than the most recently received selection input. For example, if the coder 16 elects to correct a given term, the take-back is implemented by removing the term from the terms list, the terms list is recombined according to the process flowchart in FIG. 12, and a new PCS table is created with the result. If applicable, the new PCS table determines and presents a set of corrected terminology options for review by the coder 16. As before, the corrected terminology options 810 can include those associated with character 812 of the code 801 for which there has been no selection input.

Optimizing Term Completion Look-Ahead

The term-hyperslice relationships in the HDR and the term-combination algorithm described above supports the display of possible term completion as the coder 16 enters terms. The following illustrates the method. After entering "car," the coder 16 sees the possible completions shown in FIG. 16. This figure shows screen 900, which presents to the coder 16 some but not all of the possible completions (about 30 more listings are not shown in this figure). If the coder 16 then enters "excision car," the additional information allows the system 10 to present the full set of completions in the screen 950 shown in FIG. 17.

Only those terms starting with "car," which yield a non-empty region of the PCS-n-section space when intersected with the "excision" hyperslice(s), are listed. As expected, most of these are body parts. This is accomplished by using the Search table in the HDR coupled with the term-combination algorithm. This can be done, for example, using the following steps:

Recognized terms (like "excision" in the example above) can be retained on a list, along with their associated hyperslices (recognized terms are shown in italics in the completion list).

As each character is entered past the already recognized terms, it is tracked through the Search table. Nothing is outputted until at least three characters are available.

For the third and subsequent character, the Patricia tree represented by the Search table is descended recursively. For example, after "car," every possible fourth character is considered. For each fourth character, every fifth is considered. For every fourth-fifth found, every sixth is considered, and so on.

During the recursive descent of the Patricia tree, any non-zero term-ID encountered is placed on a "tentative term list." Recursive descent ends when all nodes in the tree below those for the characters entered by the user have been visited.

For each term on the "tentative term list," its hyperslices are loaded. Those hyperslices are intersected with those belonging to the "recognized terms," using the term-combination algorithm flowcharted above.

Terms on the "tentative term list" for which the hyperslice intersections are non-empty are shown to the user as possible completions. The term text is fetched from the Terms table so it may be presented in the appropriate lower, upper or mixed case.

In some embodiments, the methods described herein are implemented using a non-transitory computer-readable medium such as a hard drive, flash drive, DVD or CD. Such a medium could include executable instructions operable to cause a computer to perform each of the enumerated steps of a given method. The present disclosure further contemplates hardware and systems for carrying out the methods described.

All patents and patent applications mentioned above are hereby expressly incorporated into the present disclosure. The foregoing invention has been described in some detail by way of illustration and example for purposes of clarity and understanding. However, various alternatives, modifications, and equivalents may be used. Accordingly, the above description should not be taken as limiting in the scope of the invention which is defined by the following claims and their equivalents.

What is claimed is:

1. A method for specifying a multi-character code implemented on a computer system having one or more processors and memories, comprising:

receiving a multi-character code having one or more unspecified characters and one or more specified characters;

receiving, via the computer system, an input term;

creating, by the computer system, a hyperslice dictionary, wherein the hyperslice dictionary comprises a plurality of multidimensional data structures;

associating, by the computer system, at least a portion of the plurality of multidimensional data structures of the hyperslice dictionary with terminology options;

providing, on a user interface, the hyperslice dictionary;

receiving, via an encoder module of the computer system and in the user interface, corrections to the hyperslice dictionary;

modifying, by the encoder module of the computer system, the hyperslice dictionary based on the corrections;

interrogating, by the encoder module of the computer system, the hyperslice dictionary using the input term;

determining, by the encoder module of the computer system, intersections in the plurality of multidimensional data structures associated with the input term and at least one of the one or more specified characters; and determining, by the encoder module of the computer system, one or more terminology options based on the intersections in the plurality of multidimensional data structures, each of the one or more determined terminology options associated with a respective one of the one or more unspecified characters.

2. The method of claim 1, further comprising:

presenting, on the user interface, the one or more terminology options;

receiving, via the user interface, a selection input associated with at least one of the one or more terminology options;

in response to receiving the selection input via the user interface:

determining, by the computer system, intersections in the plurality of multidimensional data structures associated with the search term and the selection input; and determining, by the computer system, one or more revised terminology options based on intersections in the plurality of multidimensional data structures.

3. The method of claim 2, further comprising updating the user interface to present the one or more revised terminology options.

4. The method of claim 2, wherein each of the one or more revised terminology options associated with a respective one of the one or more unspecified characters.

5. The method of claim 2, further comprising presenting in the user interface, prior to receiving the selection input, a partially or fully unspecified multi-character code.

6. The method of claim 1, wherein each character of the multi-character code, if specified, has a value selected from 0, 1, 2, 3, 4, 5, 6, 7, 8, 9, A, B, C, D, E, F, G, H, J, K, L, M, N, P, Q, R, S, T, U, V, W, X, Y, and Z.

7. The method of claim 1, wherein the hyperslice dictionary further comprises a relationship dictionary comprises relationships between input terms and the plurality of multidimensional data structures.

8. The method of claim 7, further comprising receiving one or more input terms through the user interface, wherein interrogating the hyperslice dictionary comprises considering each input term according to an order that the input term is entered.

9. The method of claim 7, wherein the relationship dictionary comprises a Patricia Tree representation of known terminology options.

10. The method of claim 1, wherein each terminology option is represented by an array of bit strings, each bit string associated with a code character and each bit of each bit string associated with a pre-defined character value.

11. The method of claim 1, further comprising: presenting on the user interface a series of questions, each question associated with a respective one of the one or more unspecified character of the multi-character code.

12. The method of claim 11, wherein the series of questions is presented in a certain order that is at least partially based on the one or more specified characters of the multi-character code.

13. A method for specifying a multi-character code implemented on a computer system having one or more processors and memories, comprising:
- receiving, via the computer system, a plurality of input terms;
- creating, by the computer system, a hyperslice dictionary, wherein the hyperslice dictionary comprises a plurality of multidimensional data structures;
- associating, by the computer system, at least a portion of the plurality of multidimensional data structures of the hyperslice dictionary with terminology options;
- providing, on a user interface, the hyperslice dictionary;
- receiving, via an encoder module of the computer system and in the user interface, corrections to the hyperslice dictionary;
- modifying, by an encoder module of the computer system, the hyperslice dictionary based on the corrections;
- interrogating, by an encoder module of the computer system, the hyperslice dictionary using the plurality of input terms;
- determining, by an encoder module of the computer system, intersections in the plurality of multidimensional data structures associated with the plurality of input terms; and
- determining, by an encoder module of the computer system, one or more terminology options based on the intersections in the plurality of multidimensional data structures, each of the one or more determined terminology options associated with a respective one character to be included in the multi-character code.

14. The method of claim 13, wherein the hyperslice dictionary further comprises a relationship dictionary comprises relationships between input terms and the plurality of multidimensional data structures.

15. The method of claim 14, further comprising receiving one or more input terms through the user interface, wherein interrogating the hyperslice dictionary comprises considering each input term according to an order that the input term is entered.

16. The method of claim 14, wherein the relationship dictionary comprises a Patricia Tree representation of known terminology options.

17. The method of claim 13, wherein each terminology option is represented by an array of bit strings, each bit string associated with a code character and each bit of each bit string associated with a pre-defined character value.

18. The method of claim 13, further comprising:
- presenting, on the user interface, the one or more terminology options;
- receiving, via the user interface, a selection input associated with at least one of the one or more terminology options;
- in response to receiving the selection input via the user interface:
  - determining, by the computer system, intersections in the plurality of multidimensional data structures associated with the search term and the selection input; and
  - determining, by the computer system, one or more revised terminology options based on intersections in the plurality of multidimensional data structures.

19. The method of claim 18, further comprising updating the user interface to present the one or more revised terminology options.

20. The method of claim 18, wherein each of the one or more revised terminology options associated with a respective one of the one or more unspecified characters.

* * * * *